(12) United States Patent
Ichihashi

(10) Patent No.: US 9,999,344 B2
(45) Date of Patent: Jun. 19, 2018

(54) ENDOSCOPE

(71) Applicant: OLYMPUS CORPORATION, Tokyo (JP)

(72) Inventor: Masaki Ichihashi, Kokubunji (JP)

(73) Assignee: OLYMPUS CORPORATION, Tokyo (JP)

( * ) Notice: Subject to any disclaimer, the term of this patent is extended or adjusted under 35 U.S.C. 154(b) by 215 days.

(21) Appl. No.: 15/073,056

(22) Filed: Mar. 17, 2016

(65) Prior Publication Data

US 2016/0192824 A1  Jul. 7, 2016

Related U.S. Application Data

(63) Continuation of application No. PCT/JP2014/063106, filed on May 16, 2014.

(30) Foreign Application Priority Data

Sep. 20, 2013 (JP) .................. 2013-195739

(51) Int. Cl.
  *A61B 1/00* (2006.01)
  *G02B 23/24* (2006.01)
  *A61B 1/05* (2006.01)
  *A61B 1/12* (2006.01)
(52) U.S. Cl.
  CPC ...... *A61B 1/00096* (2013.01); *A61B 1/00121* (2013.01); *A61B 1/00163* (2013.01); *A61B 1/05* (2013.01); *A61B 1/127* (2013.01); *G02B 23/2484* (2013.01)
(58) Field of Classification Search
  CPC ............ A61B 1/00096; A61B 1/00121; A61B 1/00163; A61B 1/05

USPC .......................................... 348/65
See application file for complete search history.

(56) References Cited

U.S. PATENT DOCUMENTS

| 6,361,491 B1 | 3/2002 | Hasegawa et al. |
| 7,282,026 B2 | 10/2007 | Ogawa |
| 2004/0030221 A1 | 2/2004 | Ogawa |

(Continued)

FOREIGN PATENT DOCUMENTS

| JP | H02-100013 A | 4/1990 |
| JP | H11-109257 A | 4/1999 |
| JP | 2000-292713 A | 10/2000 |

(Continued)

OTHER PUBLICATIONS

International Search Report dated Aug. 12, 2014 issued in PCT/JP2014/063106.

*Primary Examiner* — Jeffery Williams
(74) *Attorney, Agent, or Firm* — Scully, Scott, Murphy & Presser, P.C.

(57) ABSTRACT

An endoscope includes a lens unit, a diaphragm for brightness adjustment, a diaphragm for type determination and an image pickup device. The diaphragm for type determination has an image formation portion an image of which is formed in a light receiving section, a position and a number of the image formation portion provided for the diaphragm for type determination differing according to a plurality of adapters. The endoscope further includes a CPU that determines a type of an adapter by determining a position and a number of the image formation portion an image of which is formed in the light receiving section.

13 Claims, 13 Drawing Sheets

(56) References Cited

U.S. PATENT DOCUMENTS

2010/0188493 A1* 7/2010 Kanzaki ............ A61B 1/00059
348/75

FOREIGN PATENT DOCUMENTS

| JP | 2002-191547 A | 7/2002 |
| JP | 2003-005096 A | 1/2003 |
| JP | 2004-033487 A | 2/2004 |

* cited by examiner

ENDOSCOPE

CROSS REFERENCE TO RELATED APPLICATION

This application is a continuation application of PCT/JP2014/063106 filed on May 16, 2014 and claims benefit of Japanese Application No. 2013-195739 filed in Japan on Sep. 20, 2013, the entire contents of which are incorporated herein by this reference.

BACKGROUND OF THE INVENTION

1. Field of the Invention

The present invention relates to an endoscope in which two or more kinds of adapters are individually attachable to and detachable from a distal end portion located at a distal end in an insertion direction of an insertion portion.

2. Description of the Related Art

As is well known, endoscopes are widely used in an industrial field, for example. The endoscopes used in the industrial field are capable of performing observation of flaws, corrosion and the like in objects, and various kinds of treatment and the like by elongated insertion portions being inserted into an inside of a jet engine, insides of piping of factories or the like that are insides of objects.

A configuration is well known, in which an objective lens unit, and an image pickup unit including an image pickup device such as a CCD are provided, and an illumination unit that illuminates an inside of an object and the like are provided, in a distal end portion located at a distal end side in the insertion direction of the insertion portion of an endoscope.

Further, a configuration is also well known, in which an objective lens unit and an illumination unit are provided in a known optical adapter (hereinafter, simply called an adapter) which is attachable to and detachable from the distal end portion of an insertion portion.

Further, as an adapter, a front-view adapter for observing a front side in the insertion direction of the insertion portion, and a side-view adapter for observing a lateral side different from the insertion direction are well known, and the respective adapters are properly used in accordance with objects to be observed and use purposes.

Furthermore, in the respective front-view adapters and side-view adapters, a plurality of adapters with different viewing angles are present, and the adapters are also properly used in accordance with objects to be observed and use purposes. Further, in the respective front-view adapters and side-view adapters, a plurality of adapters with different outside diameters are present in accordance with the diameters of the distal end portions. Consequently, a plurality of kinds of adapters are individually attachable to and detachable from the distal end portion.

Further, a configuration is also well known, in which identification resistors differing in resistance value according to adapters are provided in a plurality of adapters attachable to and detachable from the distal end portion, and when an adapter is attached to the distal end portion, the identification resistor contacts a terminal for resistor identification provided in the distal end portion, whereby a control section which is electrically connected to the terminal reads the resistance value, and automatically detects the kind of the adapter attached to the distal end portion, from the resistance value.

However, when the identification resistor is provided in a limited space in an adapter, and the terminal for resistor identification is provided in a limited space in the distal end portion, there arises the problem that the adapter and the distal end portion increase in diameter.

In the light of the problem as above, Japanese Patent Application Laid-Open Publication No. 2004-33487 discloses the configuration of an endoscope system in which in the configuration where a plurality of known adapters for stereo measurement are individually attachable to and detachable from the distal end portion, two objective optical systems, and field of view masks that are located at rear sides in the respective optical axis directions of the respective objective optical systems and function as diaphragms in which openings that narrow down lights passing through the respective objective optical systems and differ in shape in accordance with the respective adapters are formed are provided in each of the respective adapters. Further, Japanese Patent Application Laid-Open Publication No. 2004-33487 discloses the configuration in which when the adapter is attached to the distal end portion, images of the lights which pass through the respective objective optical systems and the respective openings, and the field of view mask are respectively formed on the light receiving section of the image pickup device provided in the distal end portion, and two optical images and the opening shape of the field of view mask are displayed on the display section. Furthermore, Japanese Patent Application Laid-Open Publication NO. 2004-33487 discloses the configuration in which the CPU detects the opening shape of the field of view mask by image processing, and detects the kind of adapter which is attached to the distal end portion.

SUMMARY OF THE INVENTION

An endoscope according to one aspect of the present invention is an endoscope in which two or more kinds of adapters are individually attachable to and detachable from a distal end portion located at a distal end in an insertion direction of an insertion portion, including a plurality of optical members provided in each of the respective adapters, a diaphragm for brightness adjustment that is opened on an optical axis of the plurality of optical members in each of the respective adapters, a diaphragm for type determination of the adapter that is opened on the optical axis in each of the respective adapters, at a position separated from the diaphragm for brightness adjustment to sandwich at least one of the optical members between the diaphragm for type determination and the diaphragm for the brightness adjustment along the optical axis, and an image pickup device that is provided in the distal end portion, and in which an image of an object is formed in a light receiving section via the plurality of optical members in any one of the adapters attached to the distal end portion, wherein the diaphragm for type determination has an image formation portion an image of which is formed in the light receiving section of the image pickup device, and a position and a number of the image formation portion provided for the diaphragm for type determination differ according to a plurality of adapters, the endoscope further including a determination section that determines a type of each of the adapters by determining the position and the number of the image formation portion the image of which is formed in the light receiving section of the image pickup device.

DETAILED DESCRIPTION OF THE PREFERRED EMBODIMENTS

Hereinafter, embodiments of the present invention will be described with reference to the drawings. Note that an endoscope will be described with an industrial endoscope cited as an example.

First Embodiment

Figure 1:
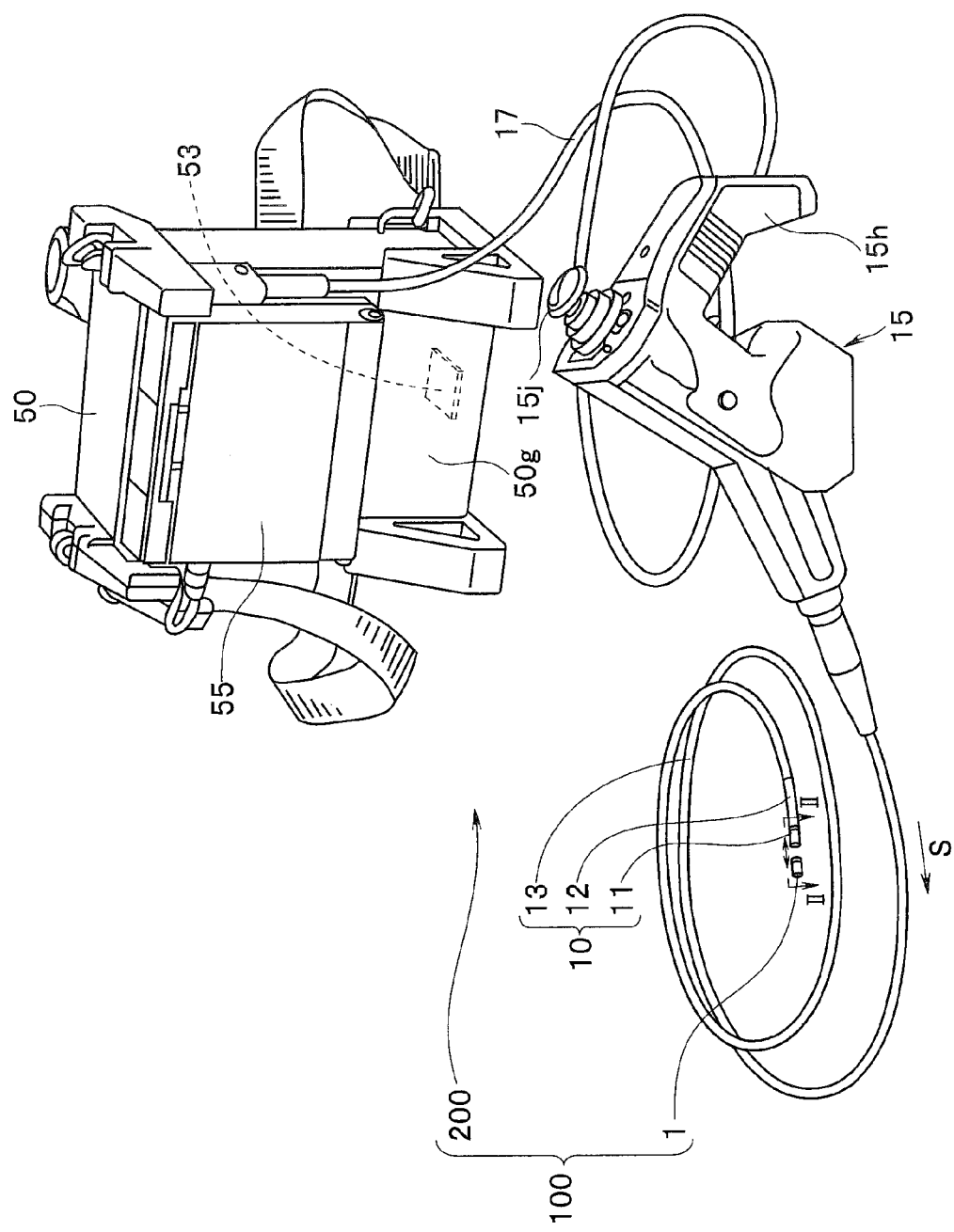
FIG. 1 is a perspective view showing a rough outline of a configuration of an endoscope system including an endoscope of a first embodiment.

FIG. 1 is a perspective view showing a rough outline of a configuration of an endoscope system including an endoscope of the present embodiment.

As shown in FIG. 1, in an endoscope system 100, a main part is configured by an endoscope 200, and two or more kinds of adapters 1. Note that hereinafter, in order to simplify the drawings and explanation, what is described as the adapter 1 is common to all of two or more kinds of adapters.

Further, in the present embodiment, two or more kinds of adapters 1 which are attachable to and detachable from the distal end portion 11 will be described with known front-view adapters cited as an example. Therefore, in the present embodiment, explanation will be made such that two or more kinds of front-view adapters having different diameters and view angles, for example, are attachable to and detachable from the distal end portion 11.

In the endoscope 200, a main part is configured by including an insertion portion 10 that is elongated and has flexibility, an operation portion 15 that is connected to a proximal end in an insertion direction S (hereinafter, simply referred to as a proximal end) of the insertion portion 10, and has a grasping portion 15h, a universal cord 17 extended from the grasping portion 15h of the operation portion 15, and an apparatus main body 50 to which an extension end of the universal cord 17 is connected.

The insertion portion 10 includes the distal end portion 11 which is located at a distal end in the insertion direction S (hereinafter, simply referred to as a distal end) of the insertion portion 10, and to or from which two or more kinds of adapters 1 are individually attachable and detachable, a bending portion 12 that is connectively provided at a proximal end of the distal end portion 11 and is bendable in four directions of an up, a down, a left and a right, for example, by an operation of a joystick 15j provided at the operation portion 15, and a long flexible tube portion 13 that is connectively provided at a proximal end of the bending portion 12 and is formed of a flexible member, and a proximal end of the flexible tube portion 13 is connected to the operation portion 15.

Note that the operation portion 15 is provided with various switches and the like not illustrated which instruct an image pickup action in an image pickup device 28 (see FIG. 2) described later and provided in the distal end portion 11, besides the joystick 15j.

The apparatus main body 50 has a box shape, for example, and a monitor 55 that displays an endoscope image that is picked up by the image pickup device 28 (see FIG. 2) is fixed to an exterior casing 50g formed by magnesium die casting, for example, to be openable and closable with respect to the exterior casing 50g, for example.

Note that the monitor 55 may be attachable to and detachable from the exterior casing 50g, or may be fixed to the exterior casing 50g in a state where a monitor face is always exposed. Further, a CPU 53 that is a determination section that determines a type of the adapter 1 attached to the distal end portion 11 is provided in the apparatus main body 50.

Figure 2:
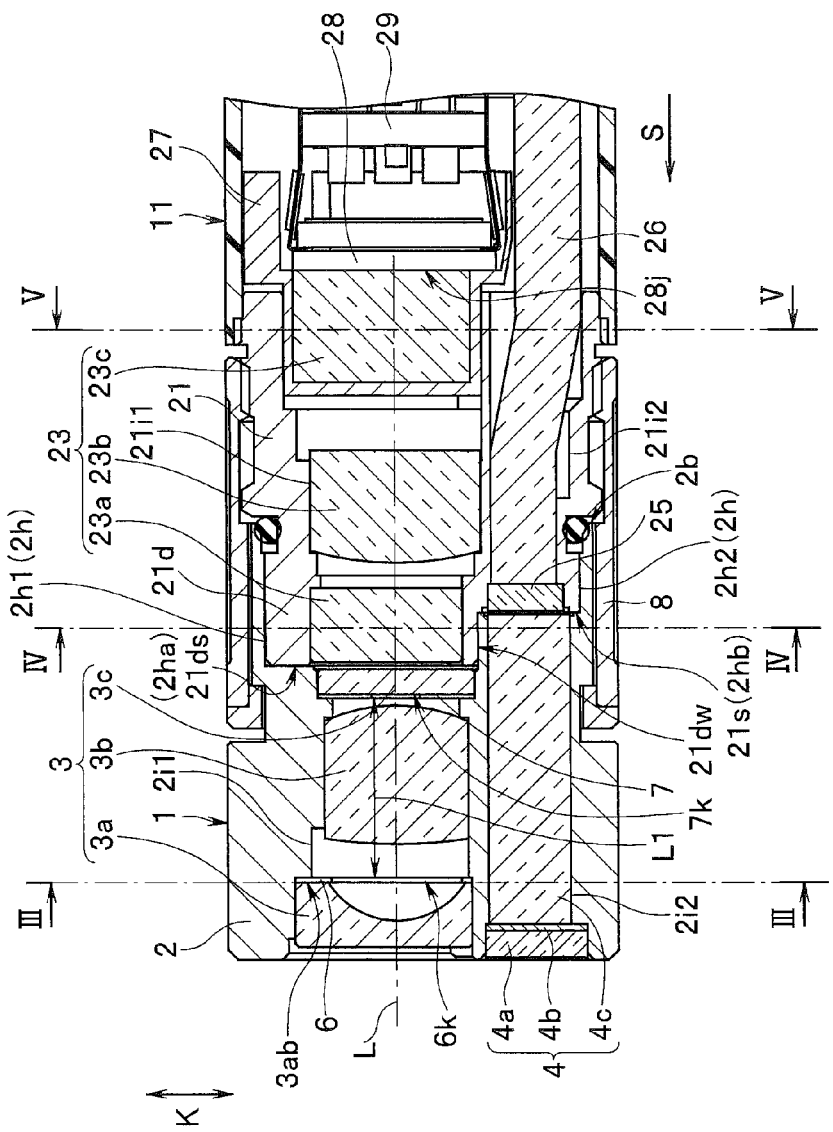
FIG. 2 is a partial sectional view along a line II-II in FIG. 1 in a state where an adapter is attached to a distal end portion of an insertion portion in FIG. 1.
Figure 3:
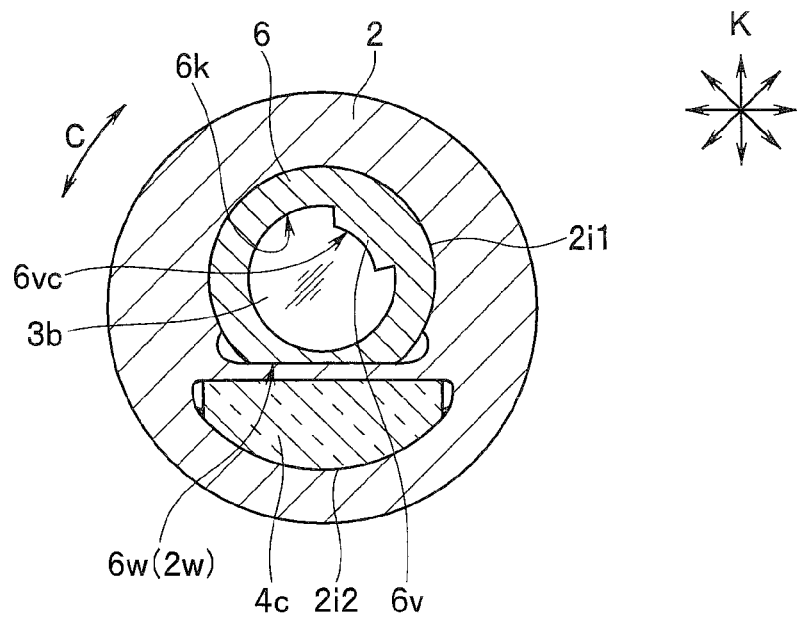
FIG. 3 is a sectional view of the adapter along a line III-III in FIG. 2.
Figure 4:
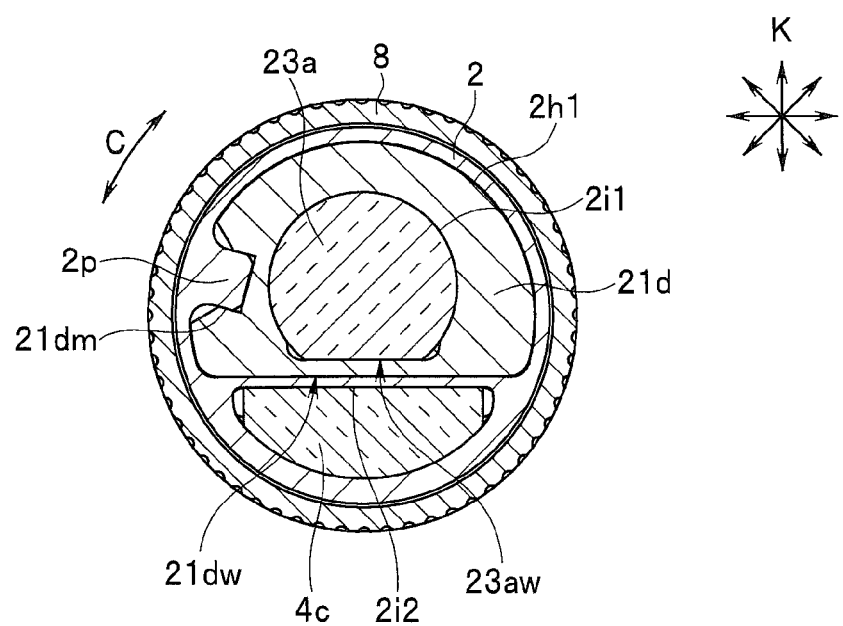
FIG. 4 is a sectional view of the distal end portion and the adapter along a line IV-IV in FIG. 2.
Figure 5:
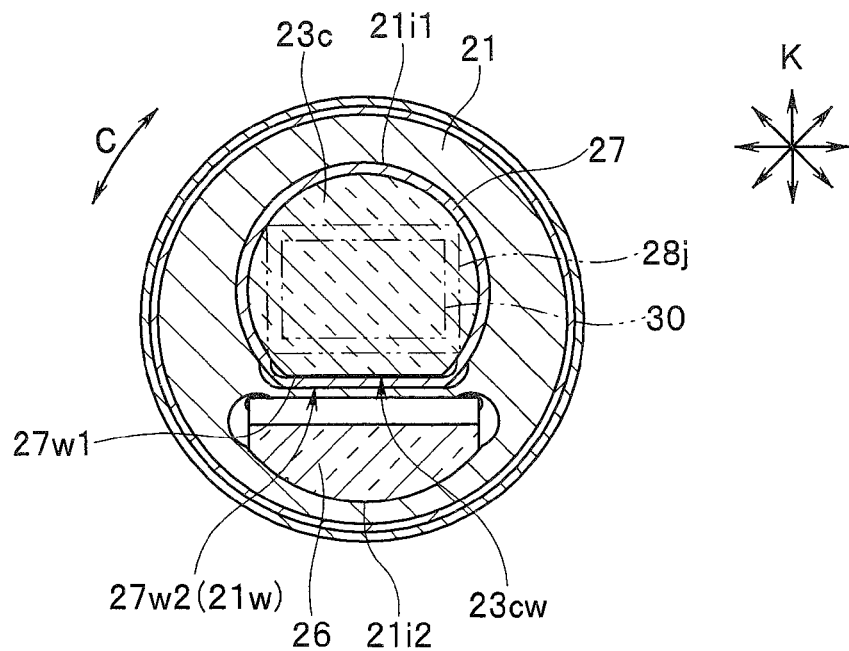
FIG. 5 is a view showing a section of the distal end portion along a line V-V in FIG. 2 with an image pickup device.

Next, a configuration of the adapter and a configuration of the distal end portion will be described with use of FIG. 2 to FIG. 11. FIG. 2 is a partial sectional view along a line II-II in FIG. 1 in a state where the adapter is attached to the distal end portion of the insertion portion in FIG. 1. FIG. 3 is a sectional view of the adapter along a line III-III in FIG. 2. FIG. 4 is a sectional view of the distal end portion and the adapter along a line IV-IV in FIG. 2. FIG. 5 is a view showing a section of the distal end portion along a line V-V in FIG. 2 with the image pickup device.

Figure 6:
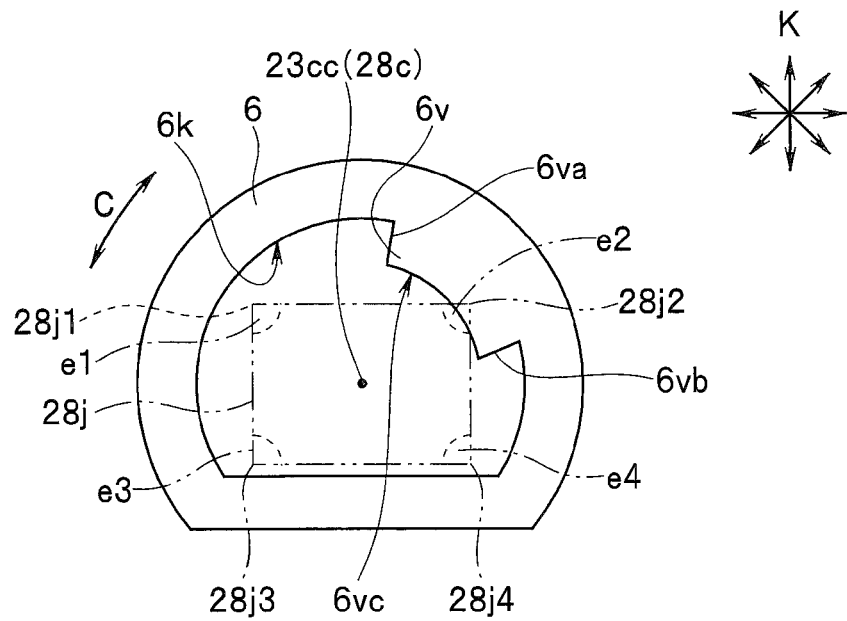
FIG. 6 is a plan view enlarging and showing a diaphragm for type determination in FIG. 2 with the image pickup device.
Figure 7:
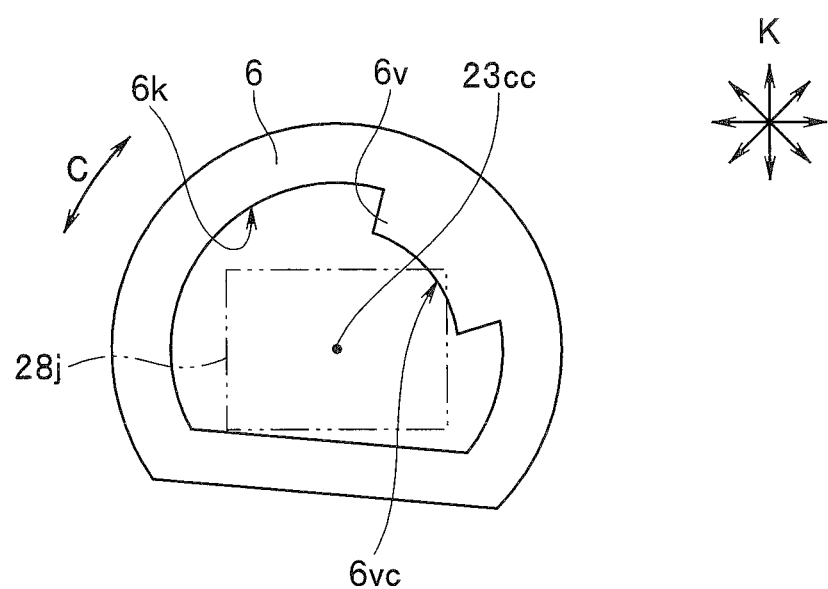
FIG. 7 is a plan view showing a state where the diaphragm for type determination in FIG. 6 is attached by being rotated in a circumferential direction of the adapter with respect to a lens frame of the adapter, with the image pickup device.
Figure 8:
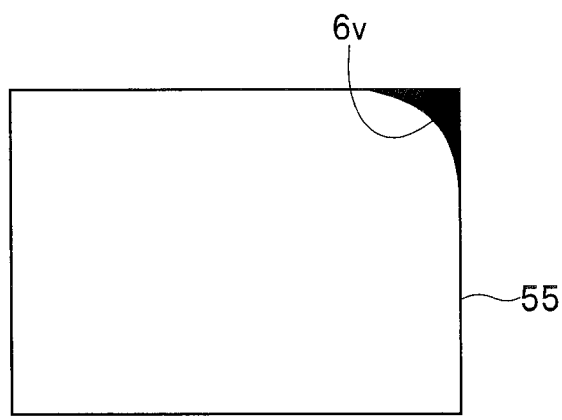
FIG. 8 is a view showing a state where an image formation portion of the diaphragm for type determination is displayed on a monitor in FIG. 1.
Figure 9:
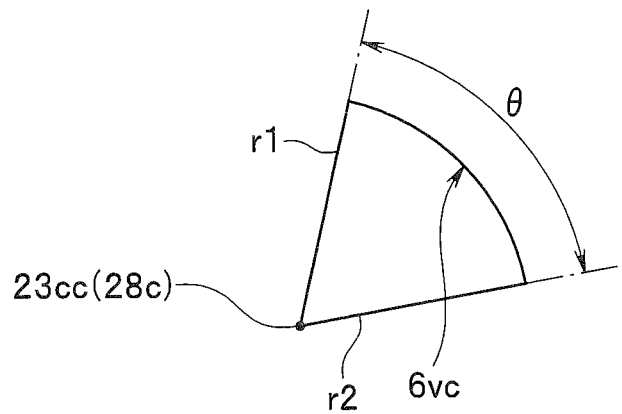
FIG. 9 is a diagram explaining angle definition of a site in a partial circular arc shape of the image formation portion in FIG. 6.

Further, FIG. 6 is a plan view enlarging and showing a diaphragm for type determination in FIG. 2 with the image pickup device. FIG. 7 is a plan view showing a state where the diaphragm for type determination is attached to a lens frame of the adapter by being rotated in a circumferential direction of the adapter, with the image pickup device. FIG. 8 is a view showing a state where an image formation portion of the diaphragm for type determination is displayed on the monitor in FIG. 1. FIG. 9 is a diagram explaining angle definition of a site in a partial circular arc shape of the image formation portion in FIG. 6.

As shown in FIG. 2, the distal end portion 11 includes a distal end portion main body 21 formed into a substantially columnar shape. On an outer circumferential face of the distal end portion main body 21, a male screw onto which a retaining ring 8 described later of the adapter 1 is screwed when the adapter 1 is attached to the distal end portion 11, is formed.

Further, on a distal end face 21s of the distal end portion main body 21, a convex portion 21d that protrudes to a front side from the distal end face 21s is formed.

The convex portion 21d is a member that performs positioning of the adapter 1 in a circumferential direction C with respect to the distal end portion 11, by being fitted to a fitting portion 2h1 in a concave portion 2h that is formed in a proximal end face 2b of a lens frame 2 that will be described later of the adapter 1 when the adapter 1 is attached to the distal end portion 11.

Note that as shown in FIG. 4, the convex portion 21d does not have a circular shape at a time of the convex portion 21d seen in plan view from an optical axis L, but has a shape in which a D cut 21dw is formed in a part of an outer circumference. Further, the adapter 1 is prevented from rotating in the circumferential direction C with respect to the distal end portion 11 when the convex portion 21d is fitted into the fitting portion 2h1, by the D cut 21dw. That is, positioning of the adapter 1 in the circumferential direction C with respect to the distal end portion 11 is performed.

Further, as shown in FIG. 4, in a part of an outer circumferential face of the convex portion 21d, a groove 21dm in which a pin 2p described later of the adapter 1 is fitted when the adapter 1 is attached to the distal end portion 11, is formed. Note that by the pin 2p being fitted into the groove 21dm, the adapter 1 is prevented from rotating in the circumferential direction C with respect to the distal end portion 11, when the convex portion 21d is fitted into the fitting portion 2h1. That is, positioning of the adapter 1 in the circumferential direction C with respect to the distal end portion 11 is also performed by fitting of the pin 2p into the groove 21dm.

Further, as shown in FIG. 2, in the distal end portion 11, a lens unit 23 that observes an inside of an object, and is configured by a plurality of lenses 23a, 23b and 23c, an image pickup device 28 such as a CCD or a C-MOS that picks up an image of the inside of the object, and an image pickup substrate 29 are provided. Note that the number of lenses configuring the lens unit 23 is not limited to three.

More specifically, in the distal end portion main body 21 and the convex portion 21d, a through-hole 21i1 that penetrates through the distal end portion main body 21 and the convex portion 21d in the insertion direction S is formed, and to the through-hole 21i1, the lens 23a and the lens 23b are fixed.

Note that in the through-hole 21i1, the lens 23a is fixed to a distal end face 21ds of the convex portion 21d to be exposed, and the lens 23b is fixed to a rear side in the insertion direction S (hereinafter, simply referred to as a rear side) from the lens 23a.

Further, as shown in FIG. 4, in a part of the outer circumference of the lens 23a, at a position facing the D cut 21dw of the convex portion 21d, a D cut 23aw parallel with the D cut 21dw is formed. That is, in the lens 23a, a shape at the time of the lens 23a seen in plan view from the optical axis L does not have a circular shape, but has a shape in which a part of the lens 23a is cut out by the D cut 23aw.

Further, a distal end side of an image pickup device fixing frame 27 in which the lens 23c is fixed is fixed to an inner circumference at a rear side from a position where the lens 23b is fixed, in the through-hole 21i1, and on a face at a proximal end side (hereinafter, simply referred to as a proximal end face) of the lens 23c, a light receiving section 28j with an external shape in a rectangular shape, more specifically, an external shape in an oblong in the image pickup device 28 is fixed to an image forming position of the lens unit 23 with high precision. Further, at a part of an outer circumference of the lens 23c, a D cut 23cw is formed as shown in FIG. 5.

Note that as shown in FIG. 5, positioning of the lens 23c in the circumferential direction C relative with respect to the light receiving section 28j is performed by the lens 23c being pasted to the light receiving section 28j in such a manner that the D cut 23cw of the lens 23c and a long side of an outline of the light receiving section 28j, or an effective pixel region 30 in an oblong with an external shape smaller than the light receiving section 28j are parallel with each other, and the D cut 23cw and a short side of the outline become orthogonal to each other, under observation by a microscope, by a worker. Note that by the above, a center 28c of the light receiving section 28j and an optical center 23cc of the lens 23c coincide with each other as shown in FIG. 6.

Further, positioning of the lens 23c in the circumferential direction C with respect to the image pickup device fixing frame 27 is performed by the lens 23c being fixed into the image pickup device fixing frame 27 in such a manner that the D cut 23cw coincides with a D cut 27w1 formed in a part of an inner circumference of the image pickup device fixing frame 27, as shown in FIG. 5.

Furthermore, positioning of the image pickup device fixing frame 27 in the circumferential direction C with respect to the distal end portion main body 21 is performed by the distal end side of the image pickup device fixing frame 27 being fixed to the distal end portion main body 21 in such a manner that a D cut 27w2 at an outer circumference of the image pickup device fixing frame 27 coincides with a D cut 21w formed by the through-hole 21i1, as shown in FIG. 5.

Note that the image pickup substrate 29 is electrically connected to the image pickup device 28, and a signal line not illustrated is extended to a rear side from the image pickup substrate 29. The signal line is inserted through insides of the insertion portion 10, the operation portion 15 and the universal cord 17, and the extension end is connected to an image processing unit and the like not illustrated in the apparatus main body 50.

Further, as shown in FIG. 2, in the distal end portion main body 21, a distal end side of a light guide 26 which is inserted through the insides of the universal cord 17, the operation portion 15 and the insertion portion 10, and a cover glass 25 are provided.

More specifically, in the distal end portion main body 21, a through-hole 21i2 that penetrates through the distal end portion main body 21 in the insertion direction S is formed, and the distal end side of the light guide 26 and the cover glass 25 are fixed to the through-hole 21i2.

Note that a distal end of the light guide 26 is butted to a proximal end face of the cover glass 25, and a face at a distal end side (hereinafter, referred to as a distal end face) of the cover glass 25 is fixed to a distal end face 21s to be exposed.

The light guide 26 guides an illuminating light irradiated from a light source not illustrated that is provided in the apparatus main body 50 to the distal end of the insertion portion 10, that is, the cover glass 25.

Further, as shown in FIG. 2, the adapter 1 includes the lens frame 2 formed into a substantially columnar shape. On the outer circumference at the proximal end side of the lens frame 2, the retaining ring 8 with a female screw formed on an inner circumferential surface is provided.

Note that when the adapter 1 is attached to the distal end portion 11, the female screw of the retaining ring 8 is screwed onto the male screw of the distal end portion main body 21 while rotating in one direction, whereby the adapter 1 is fixed to the distal end portion 11. Therefore, when the adapter 1 is rotated in the other direction, screwing of the female screw to the male screw is released, and the adapter 1 is disengaged from the distal end portion 11.

Further, in the lens frame 2, through-holes 2i1 and 2i2 that penetrate through the lens frame 2 along the insertion direction S are formed.

Further, on the proximal end face 2b of the lens frame 2, a concave portion 2h formed by being recessed to a front side along the insertion direction S from the proximal end face 2b is formed.

The concave portion 2h is configured by a fitting portion 2h2 in which the distal end side of the distal end portion main body 21 is fitted when the adapter 1 is attached to the distal end portion 11, and the fitting portion 2h1 which is formed to be recessed to the front side from the fitting portion 2h2 and into which the convex portion 21d is fitted.

Note that the fitting portion 2h1 communicates with the through-hole 2i1, and the fitting portion 2h2 communicates with the through-hole 2i2.

Further, when the adapter 1 is attached to the distal end portion 11, the distal end face 21ds of the convex portion 21d abuts on a bottom face 2ha of the fitting portion 2h1, and the distal end face 21s of the distal end portion main body 21 faces a bottom face 2hb of the fitting portion 2h2.

Furthermore, as shown in FIG. 4, in a proximal end side of the lens frame 2, the pin 2p that protrudes inward in a radial direction K toward the fitting portion 2h1 is provided at a part of a site where the fitting portion 2h1 is formed. The pin 2p is fitted into the groove 21dm which is formed on an outer circumferential face of the distal end portion main body 21, after the female screw of the adapter 1 is screwed onto the male screw of the distal end portion main body 21.

Further, in the through-hole 2i1, a lens unit 3 configured by lenses 3a, 3b and 3c that are a plurality of optical members and observes an inside of an object, more specifically, a front side with respect to the adapter 1 is fixed so that the lens 3a is exposed to the distal end face of the adapter 1. Note that the number of lenses configuring the lens unit 3 is not limited to three.

Consequently, when the adapter 1 is attached to the distal end portion 11, an image of an observation site in the object is formed on the light receiving section 28j of the image pickup device 28 via the lens unit 3 and the lens unit 23.

Further, in the through-hole 2i2, an illumination optical system 4 which is configured by a rod lens 4c that is elongated along the insertion direction S, a ball lens 4b that abuts on a distal end face of the rod lens 4c, and a cover glass 4a that abuts on a distal end face of the ball lens 4b and is exposed to the distal end face of the adapter 1 is fixed.

The illumination optical system 4 receives an illuminating light irradiated from the distal end of the cover glass 25 when the adapter 1 is attached to the distal end portion 11, and supplies the illuminating light to the object. More specifically, the rod lens 4c guides the illuminating light emitted from the cover glass 25 to the ball lens 4b. The ball lens 4b diffuses and irradiates the illuminating light into the object. The cover glass 4a protects the ball lens 4b.

Here, as shown in FIG. 2 and FIG. 3, in the through-hole 2i1, a diaphragm for brightness adjustment (hereinafter, simply referred to as a diaphragm) 7 that adjusts an observation depth is fixed to a distal end face of the lens 3c. Note that the diaphragm 7 has an opening 7k that is opened on an optical axis L of the lens unit 3. Further, a position where the diaphragm 7 is fixed is not limited to the distal end face of the lens 3c, but the diaphragm 7 may be fixed to the through-hole 2i1 in any position.

Further, in the through-hole 2i1, a diaphragm for type determination (hereinafter, simply referred to as a diaphragm) 6 of the adapter 1 is fixed to a position away from the diaphragm 7 along the optical axis L, more specifically, a position separated to a front side which is an object side from the diaphragm 7 along the optical axis L so as to sandwich the lens 3b with the diaphragm 7 along the optical axis L, on the optical axis L, much more specifically, a position that abuts on a proximal end face 3ab of the lens 3a that is separated to a front side by L1 from the diaphragm 7.

Note that the position where the diaphragm 6 is fixed is not limited to the position that abuts on the proximal end face 3ab of the lens 3a, but may be any place in the through-hole 2i1 as long as the position is separated from the diaphragm 7 along the optical axis L to sandwich at least one lens with the diaphragm 7, or the diaphragm 6 may be provided at a rear side from the diaphragm 7.

The diaphragm 6 is formed by copper foil being etched, for example, to have an opening 6k which is opened on the optical axis L.

Further, as shown in FIG. 3, in the diaphragm 6, a shape at the time of the diaphragm 6 being seen in plan view along the optical axis L does not have a circular shape, and the diaphragm 6 is formed into a shape in which a D cut 6w is formed in a part of an outer circumference.

Note that positioning of the diaphragm 6 in the circumferential direction C with respect to the lens frame 2 is performed by the diaphragm 6 being fixed to the through-hole 2i1 so that the D cut 6w coincides with the D cut 2w which is formed by the through-hole 2i1, as shown in FIG. 3.

That is, positioning of the diaphragm 6 in the circumferential direction C with respect to the light receiving section 28j when the adapter 1 is attached to the distal end portion 11 is defined by five positionings by the positioning of the diaphragm 6 in the circumferential direction C with respect to the lens frame 2 by causing the D cut 2w and the D cut 6w to coincide with each other, the positioning of the image pickup device fixing frame 27 in the circumferential direction C with respect to the distal end portion main body 21 by causing the D cut 21w and the D cut 27w2 to coincide with each other, the positioning of the lens 23c in the circumferential direction C with respect to the image pickup device fixing frame 27 by causing the D cut 27w1 and the D cut 23cw to coincide with each other, the positioning of the lens 23c in the circumferential direction C to the light receiving section 28j by causing the D cut 23cw and the outline of the light receiving section 28j or the effective pixel region 30 to coincide with each other, and the positioning of the adapter 1 in the circumferential direction C with respect to the distal end portion 11 by the pin 2*p* being fitted into the groove 21*dm*, as described above.

Further, in the present embodiment, the diaphragm 6 functions as a flare diaphragm that removes unnecessary light by narrowing down the light forming an image in the light receiving section 28*j* of the image pickup device 28 via the lens unit 3, more specifically, prevents flare from being generated as a result that light from outside a field of view, and light from outside the field of view, which is reflected by the lens frame 2 or the like are incident on the light receiving section 28*j*. Note that a thickness of the diaphragm 6, and the number of diaphragms 6 are adjusted, and thereby focusing to the light receiving section 28*j* is performed.

Furthermore, as shown in FIG. 3, the diaphragm 6 has an image formation portion 6*v* an image of which is formed in the light receiving section 28*j* by protruding to the opening 6*k*.

Note that the reason why the diaphragm 6 is provided by being separated from the diaphragm 7 by L1 along the optical axis L as described above is that if the diaphragm 6 is provided close to the diaphragm 7, an image of the outline of the image formation portion 6*v* is formed in a blurred state when the image of the image formation portion 6*v* is formed in the light receiving section 28*j*, and determination of the image formation portion 6*v* described later by the CPU 53 is difficult to perform.

This is because since the diaphragm 7 is a diaphragm for brightness adjustment, a light flux passing through the opening 6*k* becomes thinner as the diaphragm 7 is farther away from the diaphragm 6 along the optical axis L, that is, the diaphragm 6 is farther away from the diaphragm 7, focus is more sharpened, and therefore, the image of the outline of the image formation portion 6*v* provided in the diaphragm 6 is readily formed clearly in the light receiving section 28*j*.

Note that in the present embodiment, as shown in FIG. 6, the image formation portion 6*v* is shown with the case cited as an example, in which the image formation portion 6*v* is formed in a position overlapping a region e2 in a corner portion including a corner portion 28*j*2 of the light receiving section 28*j*, that is, a position where the image is formed in the region e2, with respect to the diaphragm 6, in the state where the external shape center of the diaphragm 6, and a center 28*c* (an optical center 23*cc* of the lens 23*c*) of the light receiving section 28*j* coincide with each other.

However, the image formation portion 6*v* can be provided for the diaphragm 6, in at least one of a position overlapping a region e1 in a corner portion including a corner portion 28*j*1 of the light receiving section 28*j*, that is, a position where the image is formed in the region e1, the position overlapping the region e2 in the corner portion, that is, the position where the image is formed in the region e2, a position overlapping a region e3 in a corner portion including a corner portion 28*j*3 of the light receiving section 28*j*, that is, a position where the image is formed in the region e3, and a position overlapping a region e4 in a corner portion including a corner portion 28*j*4 of the light receiving section 28*j*, that is, a position where the image is formed in the region e4.

Note that the position where the image formation portion 6*v* is provided, and the number of image formation portions 6*v*, for the diaphragm 6 differ according to a plurality of adapters 1.

Further, the CPU 53 provided in the apparatus main body 50 has a function of determining a type of the adapter 1 attached to the distal end portion 11 by detecting the position and the number of image formation portions 6*v* images of which are formed in the light receiving section 28*j* by performing image processing, and displaying a determination result on the monitor 55. Note that at this time, if the image of the image formation portion 6*v* is clearly formed in the light receiving section 28*j* as described above, the CPU 53 does not erroneously detect the position and the number of image formation portions 6*v*.

Further, the CPU 53 can determine $2^4=16$ types of adapters 1 which are attached to the distal end portion 11 by determining the position and the number of the image formation portions 6*v* the images of which are formed in the regions e1 to e4 in the four corners of the light receiving section 28*j*, that is, by determining presence or absence of the image formation portion 6*v* for the respective regions e1 to e4.

However, when all of the regions e1 to e4 in the four corners are in a state where no image of the image formation portion 6*v* is formed, the CPU 53 determines that the adapter is in a state of being unattached to the distal end portion 11, without determining the type of the adapter 1, and displays notification to that effect on the monitor 55.

This is because when the image of the image formation portion 6*v* is not formed in any of the regions e1 to e4, it can be determined that the adapter 1 is detached from the distal end portion 11 during observation, or the adapter 1 is not attached to the distal end portion 11 from the beginning.

Further, when the images of the image formation portion 6*v* are formed in all of the regions e1 to e4 in the four corners, the CPU 53 does not determine the type of the adapter 1. This is because when the images of the image formation portion 6*v* are formed in all of the regions e1 to e4, the amount of light incident on the light receiving section 28*j* becomes insufficient, and therefore, the CPU 53 is apt to erroneously recognizes the case where the images of the image formation portion 6*v* are formed in all of the regions e1 to e4, and a case where the inside of an object is dark.

That is, the CPU 53 can determine 14 types of adapters 1 to be attached to the distal end portion 11, which are obtained by subtracting the aforementioned two types from 16 types.

Further, as shown in FIG. 3 and FIG. 6, the image formation portion 6*v* has a site 6*vc* in a partial circular arc shape with the center 28*c* of the light receiving section 28*j* as a center of the circle. That is, a center of the site 6*vc* coincides with the centers 28*c* and 23*cc*.

Further, as shown in FIG. 6 and FIG. 9, a length of the circular arc shape in the circumferential direction C of the site 6*vc* is defined by an angle θ that is formed by a line r1 and a line r2 when respective end portions 6*va* and 6*vb* in the circumferential direction C of the image formation portion 6*v* and the center 28*c* of the light receiving section 28*j* are respectively connected by the lines r1 and r2.

Note that since the image formation portion 6*v* has the site 6*vc* in the partial circular arc shape, the image formation portion 6*v* is displayed with the circular arc shape at an upper right side of the monitor 55, as shown in FIG. 8, when the image formation portion 6*v* is provided in the position where the image is formed on the region e2 as shown in FIG. 6.

Consequently, when the image formation portion 6*v* is provided in the position where the image is formed in the region e1, the image formation portion 6*v* is displayed with the circular arc shape at an upper left side of the monitor 55. When the image formation portion 6*v* is provided in the position where the image is formed in the region e3, the image formation portion 6*v* is displayed with the circular arc shape at a lower left side of the monitor 55. When the image formation portion 6v is provided in the position where the image is formed in the region e4, the image formation portion 6v is displayed with the circular arc shape at a lower right side of the monitor 55.

The image formation portion 6v is displayed on the monitor 55 as above, whereby an operator can also easily recognize the type of the adapter 1 visually from the positions and the number of the image forming portions 6v displayed on the monitor 55. Note that even when the image formation portion 6v is not displayed on the monitor 55, the determination result of the CPU 53 is displayed on the monitor 55, and therefore, the operator can easily recognize the type of the adapter 1 visually.

Note that the reason why the image formation portion 6v has the site 6vc in the partial circular arc shape is that even if the diaphragm 6 is fixed by being displaced in the circumferential direction C with respect to the through-hole 2i1, that is, even if the diaphragm 6 is fixed by being displaced in the circumferential direction C with respect to the light receiving section 28j, as shown in FIG. 7, the center 28c of the light receiving section 28j and the external shape center of the diaphragm 6 coincide with each other, and therefore the shape of the image of the image formation portion 6v, which is formed in the light receiving section 28j becomes the same if the site 6vc in the circular arc shape is provided. In other words, this is because even if the diaphragm 6 is fixed to the through-hole 2i1 in a state where the position of the diaphragm 6 is displaced in the circumferential direction C, an image of the outline of the image formation portion 6v is caused to be reliably formed in the light receiving section 28j.

Consequently, the angle θ of the site 6vc shown in FIG. 9 needs to be set to be larger than a value obtained by adding up of an error in the positioning of the diaphragm 6 in the circumferential direction C with respect to the lens frame 2, an error in the positioning of the image pickup device fixing frame 27 in the circumferential direction C with respect to the distal end portion main body 21, an error in the positioning of the lens 23c in the circumferential direction C with respect to the image pickup device fixing frame 27, an error in the positioning of the lens 23c in the circumferential direction C with respect to the light receiving section 28j, and an error in the positioning of the adapter 1 in the circumferential direction C with respect to the distal end portion 11, which are defined in the positioning of the diaphragm 6 in the circumferential direction C with respect to the light receiving section 28j. This is because if the angle θ is set to be smaller than the value obtained by the aforementioned five errors being added up, the image of the image formation portion 6v is not formed in the light receiving section 28j after the diaphragm 6 is assembled, due to the positioning errors in the circumferential direction C.

Here, the aforementioned regions e1 to e4 in the four corners of the light receiving section 28j optically have large aberrations and distortion, have low image forming performance, and become dark portions because the illuminance of reflected light of illuminating light becomes lower radially from a center of the reflected light, and therefore, the regions e1 to e4 have deteriorated image qualities which are not used in observation of an ordinary object in many cases.

Consequently, in the present embodiment, the regions e1 to e4 with the deteriorated image qualities are not used in observation of an object, but used as the image formation regions of the image formation portion 6v for determining the type of the adapter 1, and therefore, even if the image of the image formation portion 6v is formed in the light receiving section 28j, the type of the adapter 1 can be determined without affecting observation of the object.

Figure 10:
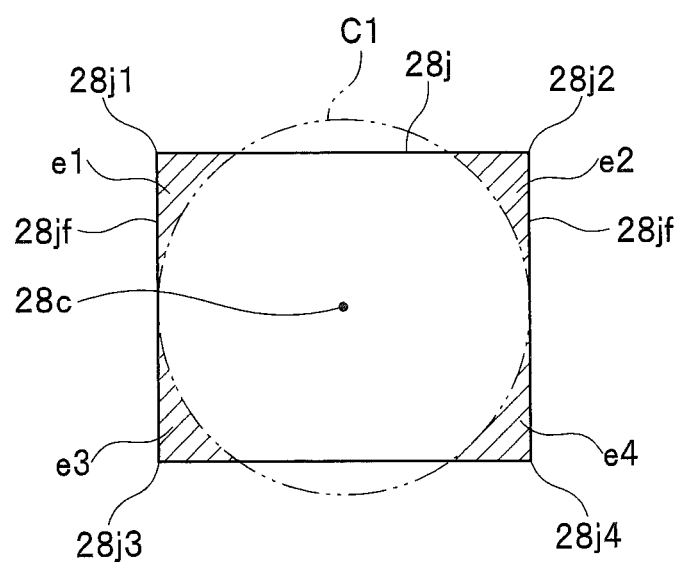
FIG. 10 is a view explaining regions in four corners on which an image of the image formation portion of the adapter is formed, in a light receiving section of the image pickup device in FIG. 2.
Figure 11:
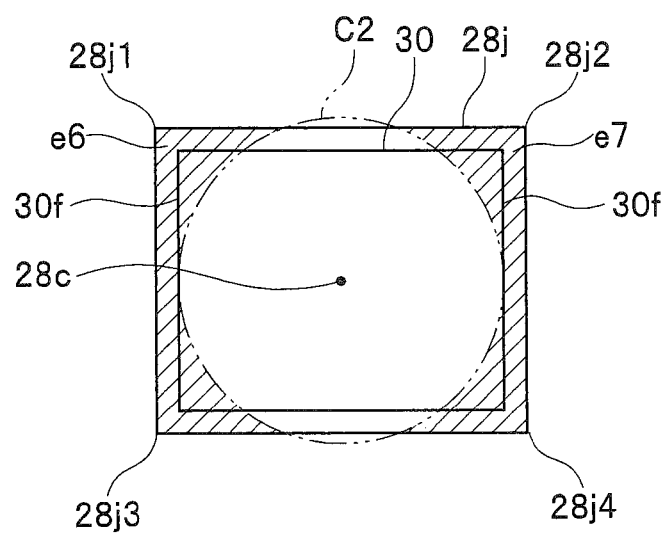
FIG. 11 is a view explaining regions in four corners where the image of the image formation portion of the adapter is formed, which are different from FIG. 10, in the light receiving section of the image pickup device in FIG. 2.

Note that hereinafter, a specific setting method of the regions in the four corners to the light receiving section 28j will be shown with use of FIG. 10 and FIG. 11. FIG. 10 is a view explaining the regions in the four corners on which the image of the image formation portion of the adapter is formed, in the light receiving section of the image pickup device in FIG. 2. FIG. 11 is a view explaining the regions in the four corners on which the image of the image formation portion of the adapter is formed, in the light receiving section of the image pickup device in FIG. 2, which are different from the regions in FIG. 10.

As shown in FIG. 10, the regions e1 to e4 in the four corners are set at four regions respectively made as shown by oblique lines in FIG. 10 between an inscribed circle C1 that has the center 28c of the light receiving section 28j as a center of the circle and inscribes a short side 28jf of the light receiving section 28j having the oblong external shape, and the four corners 28j1 to 28j4 of the light receiving section 28j.

Further, as shown in FIG. 11, the regions e1 to e4 in the four corners may be set within two regions (e6, e7) that are respectively made as shown by oblique lines in FIG. 11 between an inscribed circle C2 that has the center 28c of the light receiving section 28j as a center of the circle, and inscribes a short side 30f of a use pixel region 30 which has a smaller external shape than the light receiving section 28j and has an oblong external shape, and the four corners 28j1 to 28j4 of the light receiving section 28j.

Note that although in the case of FIG. 11, the image of the image formation portion 6v which is formed outside the use pixel region 30 in the light receiving section 28j is not displayed on the monitor 55, image processing of the image formation portion 6v by the CPU 53 is not affected, and therefore, even in this case, the CPU 53 can reliably perform determination of the image formation portion 6v.

Further, in recent years, the number of pixels has been increased by reducing pixel pitches in the light receiving sections in the image pickup devices for use in endoscopes, and if the pixel pitches are reduced, the problem that observation depth becomes shallow arises. Thus, a configuration that does not use all of the regions of the light receiving section 28j can be adopted in order to make the observation depth large, and in the configuration like this, the setting method of the regions e6 and e7 shown in FIG. 11 is suitable.

As above, in the present embodiment, it is shown that the CPU 53 determines the positions and the number of the images of the image formation portion 6v in the diaphragm 6 provided in the adapter 1, which are formed in the regions e1 to e4 in the four corners of the light receiving section 28j, whereby the type of the adapter 1 attached to the distal end portion 11 is determined.

Further, it is shown that in the adapter 1, the diaphragm 6 having the image formation portion 6v is provided by being separated by L1 along the optical axis L from the diaphragm 7 for brightness adjustment so as to sandwich the lens 3b between the diaphragm 6 and the diaphragm 7.

According to the above, in the respective regions e1 to e4 of the light receiving section 28j, the image of the outline of the image formation portion 6v is clearly formed, and therefore, after image processing, the CPU 53 does not erroneously recognize the position and the number of image formation portions 6v, so that recognition ability for the image formation portion 6v by the CPU 53 can be enhanced.

Further, in the present embodiment, it is shown that the image formation portion 6v has the site 6vc in the partial circular arc shape having the center 28c of the light receiving section 28j as the center of the circle.

According to the above, even if the diaphragm 6 is fixed by being displaced in the circumferential direction C with respect to the through-hole 2i1, as shown in FIG. 7, that is, even if the diaphragm 6 is fixed by being displaced in the circumferential direction C with respect to the light receiving section 28j, the image of the outline of the site 6vc in the partial circular arc shape of the image formation portion 6v can be reliably formed in the light receiving section 28j, because the center 28c of the light receiving section 28j and the outline center of the diaphragm 6 coincide with each other.

Further, it is shown that the angle θ of the site 6vc is set to be larger than the value by adding up of the error in the positioning of the diaphragm 6 in the circumferential direction C with respect to the lens frame 2, the error in the positioning of the image pickup device fixing frame 27 in the circumferential direction C with respect to the distal end portion main body 21, the error in the positioning of the lens 23c in the circumferential direction C with respect to the image pickup device fixing frame 27, the error in the positioning of the lens 23c in the circumferential direction C with respect to the light receiving section 28j, and the error in the positioning of the adapter 1 in the circumferential direction C with respect to the distal end portion 11, which are defined in the positioning of the diaphragm 6 in the circumferential direction C with respect to the light receiving section 28j.

According to the above, even if the aforementioned five positioning errors occur in the circumferential direction C, the image of the outline of the site 6vc in the partial circular arc shape of the image formation portion 6v can be reliably formed in the respective regions e1 to e4 of the light receiving section 28j.

From the above, the endoscope 200 can be provided, which includes the configuration that can accurately and easily detect the type of the adapter 1 from the diaphragm 6 the image of which is formed in the light receiving section 28j.

Figure 12:
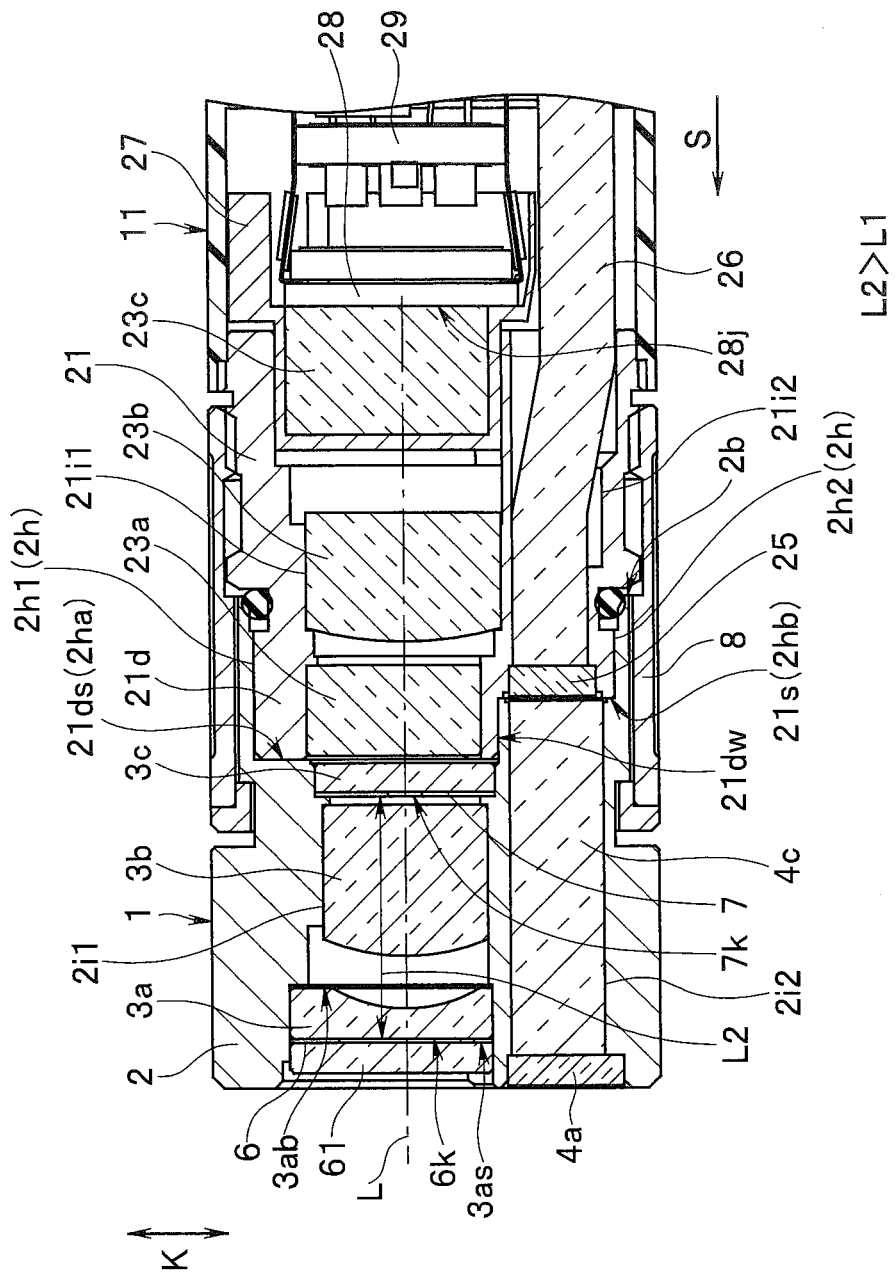
FIG. 12 is a partial sectional view of a modification in which at a distal end face of an objective lens of a lens unit provided in the adapter in FIG. 2, the diaphragm for type determination is provided by being inserted between the distal end face of the objective lens and a cover glass.

Note that hereinafter, a modification will be shown with use of FIG. 12. FIG. 12 is a partial sectional view showing the modification in which on a distal end face of an objective lens of a lens unit provided in the adapter in FIG. 2, a diaphragm for type determination is provided by being inserted between the distal end face of the objective lens and a cover glass.

In the present embodiment described above, it is shown that in the through-hole 2i1, the diaphragm 6 is fixed so as to abut on the proximal end face 3ab of the objective lens 3a.

As shown in FIG. 12, the diaphragm 6 may be fixed to the through-hole 2i1 to abut on a distal end face 3as of the objective lens 3a, without being limited to the above. Further, in the configuration like this, dust, oil or the like is likely to adhere to the diaphragm 6, if the diaphragm 6 is exposed onto the distal end face of the adapter, and therefore, the diaphragm 6 is preferably fixed by being inserted between the distal end face 3as of the objective lens 3a and a cover glass 61 that prevents dirt and the like from adhering to the diaphragm 6. That is, the cover glass 61 is exposed on the distal end face of the adapter 1.

According to the configuration as above, since the diaphragm 6 is fixed to abut on the distal end face 3as, a separation distance L2 from the diaphragm 7 in the optical axis L is long (L2>L1) as compared to the case where the diaphragm 6 is fixed to abut on the proximal end face 3ab as in the present embodiment described above, and therefore, the image of the image formation portion 6v of the diaphragm 6 is more clearly formed on the regions e1 to e4 in the four corners of the light receiving section 28j. Hence, determination of the image formation portion 6v by the CPU 53 can be enhanced more than the determination in the present embodiment described above. Note that the other configurations and effects are the same as the configurations and the effects in the present embodiment described above.

Figure 13:
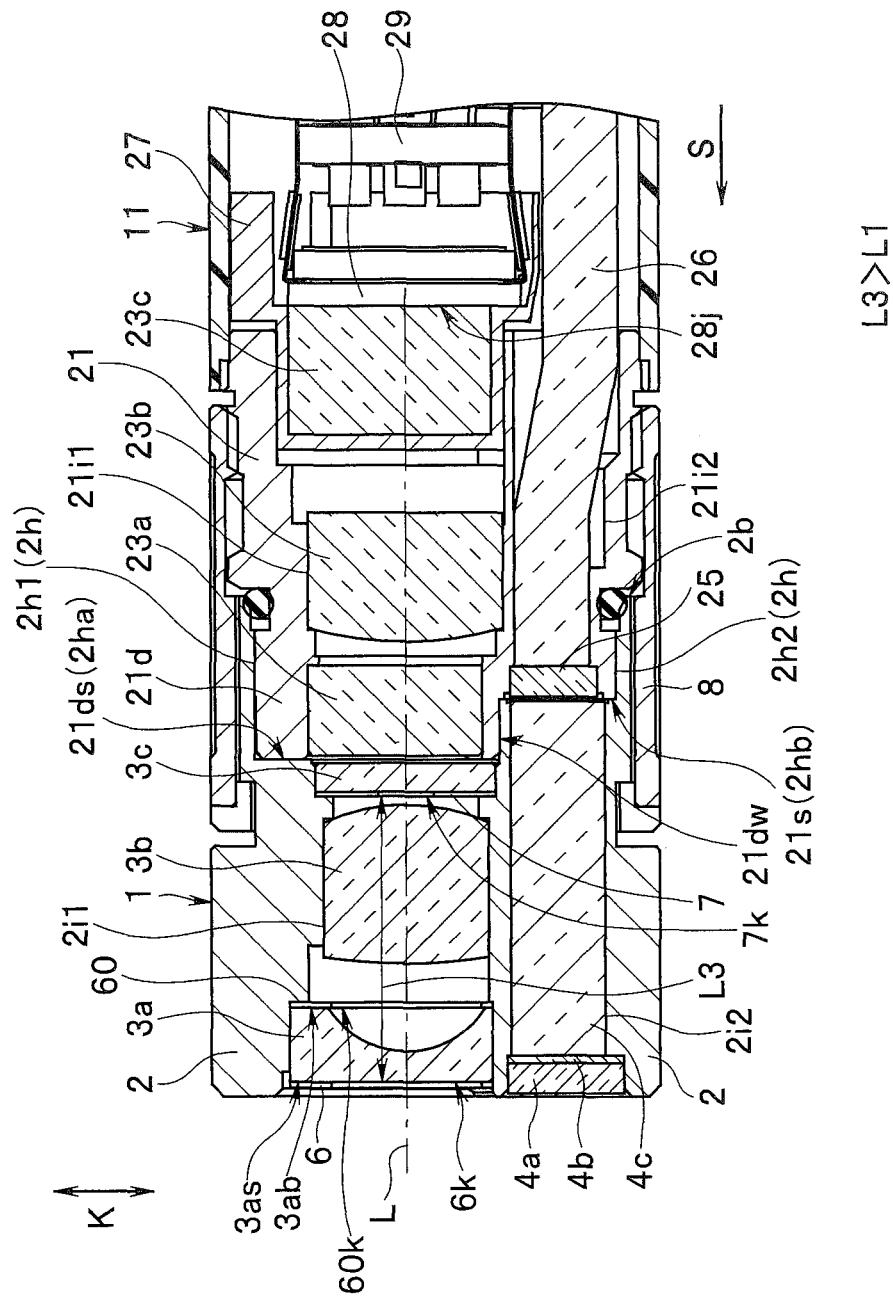
FIG. 13 is a partial sectional view showing a modification in which at the distal end face of the objective lens of the lens unit provided in the adapter in FIG. 2, a diaphragm for type determination is provided separately from a flare diaphragm.

Note that hereinafter, another modification will be shown with use of FIG. 13. FIG. 13 is a partial sectional view showing a modification in which on the distal end face of the objective lens of the lens unit provided in the adapter in FIG. 2, a diaphragm for type determination is provided separately from a flare diaphragm.

In the present embodiment described above, it is shown that the diaphragm 6 for type determination functions as a flare diaphragm that removes unnecessary light when the adapter 1 is attached to the distal end portion 11.

The flare diaphragm is not limited to the above, and as shown in FIG. 13, a flare diaphragm 60 that has an opening 60k that opens to the optical axis L and removes unnecessary light by narrowing down the light forming the image in the light receiving section 28j via the lens unit 3 may be fixed to the proximal end face 3ab of the objective lens 3a separately from the diaphragm 6 for type determination, whereas the diaphragm 6 for type determination may be fixed to the distal end face 3as of the objective lens 3a separately from the flare diaphragm 60.

According to the configuration as above, a separation distance L3 from the diaphragm 7 in the optical axis L becomes long (L3>L1), as compared with the case where the diaphragm 6 is fixed to abut on the proximal end face 3ab as in the present embodiment described above, similarly to FIG. 12, and therefore, the image of the image formation portion 6v of the diaphragm 6 is more clearly formed in the regions e1 to e4 in the four corners of the light receiving section 28j. From this, determination of the image formation portion 6v by the CPU 53 can be enhanced more than in the present embodiment described above.

Further, in the configuration shown in FIG. 13, the diaphragm 6 may be integrally formed by vapor deposition to the distal end face 3as.

According to the above, production cost can be reduced more than in the configuration shown in FIG. 12, because the diaphragm 6 can be formed to be thinner along the optical axis L than in the present embodiment described above, while dust hardly accumulates in the diaphragm 6 and oil hardly soaks into the diaphragm 6 even without the cover glass 61. Note that the other configurations and effects are the same as in the present embodiment described above.

Second Embodiment

Figure 14:
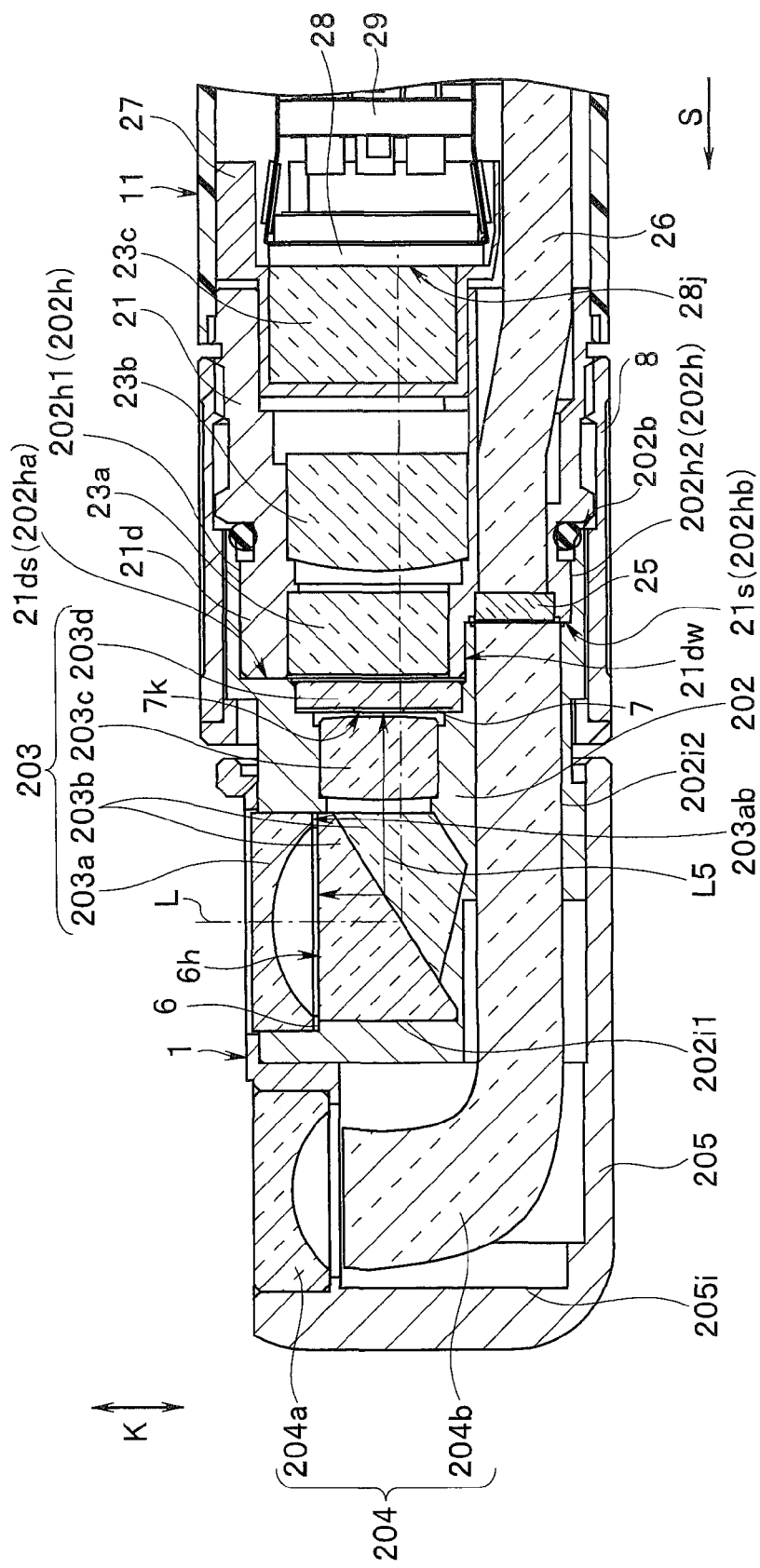
FIG. 14 is a partial sectional view in a state where an adapter is attached to a distal end portion of an insertion portion of an endoscope of a second embodiment.

FIG. 14 is a partial sectional view in a state where an adapter is attached to a distal end portion of an insertion portion of an endoscope of a present embodiment.

A configuration of an endoscope of a second embodiment differs in that an adapter attachable to and detachable from the distal end portion of the insertion portion is a known side-view adapter, as compared with the endoscope of the first embodiment shown in FIG. 1 to FIG. 11 described above. Consequently, only the difference will be described, the same components as the components of the first embodiment are assigned the same reference signs, and explanation of the components will be omitted.

Consequently, in the present embodiment, as the two or more kinds of adapters 1 attachable to and detachable from the distal end portion 11 will be described with side-view adapters cited as examples. Further, in the present embodiment, explanation will be made such that two or more kinds of side-view adapters with different diameters and view angles, for example, are attachable to and detachable from the distal end portion 11.

As shown in FIG. 14, the adapter 1 which is used in the present embodiment includes a lens frame 202 formed into a substantially columnar shape. On an outer circumference at a proximal end side of the lens frame 202, the retaining ring 8 having a female screw formed on an inner circumferential face is provided.

On a proximal end face 202*b* of the lens frame 202, a concave portion 202*h* that is formed to be recessed to a front side along the insertion direction S from the proximal end face 202*b* is formed.

The concave portion 202*h* is configured by a fitting portion 202*h*2 into which the distal end side of the distal end portion main body 21 is fitted when the adapter 1 is attached to the distal end portion 11, and a fitting portion 202*h*1 that is formed to be recessed to a front side from the fitting portion 202*h*2 and into which the convex portion 21*d* is fitted.

Further, the distal end face 21*ds* of the convex portion 21*d* abuts on a bottom face 202*ha* of the fitting portion 202*h*1 when the adapter 1 is attached to the distal end portion 11, and the distal end face 21*s* of the distal end portion main body 21 faces a bottom face 202*hb* of the fitting portion 202*h*2.

Furthermore, in the proximal end side of the lens frame 202, at a part of a site where the fitting portion 202*h*1 is formed, a pin not illustrated that protrudes inward in the radial direction K toward the fitting portion 202*h*1 is provided as shown in FIG. 4 of the aforementioned first embodiment. The pin is fitted into the groove 21*dm* (see FIG. 4) formed on the outer circumferential face of the distal end portion main body 21 after the female screw of the adapter 1 is screwed onto the male screw of the distal end portion main body 21.

Further, an L-shaped through-hole 202*i*1 that has one end opened to one side face of the outer circumferential face of the adapter 1, and the other end opened to the fitting portion 202*h*1 is formed in the lens frame 202.

Further, in the through-hole 202*i*1, a lens unit 203 that is configured by a lens 203*a*, a prism 203*b*, a lens 203*c* and a lens 203*d* that are a plurality of optical members, and observes an inside of an object, more specifically, an observation site located at the radial direction K side with respect to the adapter 1 is fixed in such a manner that the lens 203*a* is exposed on one side face of the outer circumferential face of the adapter 1. Note that the number of lenses configuring the lens unit 203 is not limited to three.

Therefore, when the adapter 1 is attached to the distal end portion 11, an image of the observation site in the object is formed in the light receiving section 28*j* of the image pickup device 28 via the lens unit 203 and the lens unit 23.

Furthermore, in the lens frame 202, a through-hole 202*i*2 that penetrates through the lens frame 202 in the insertion direction S is formed.

Further, the outer circumference at the distal end side of the lens frame 202 is covered with a cover member 205. In the cover member 205, an L-shaped through-hole 205*i* having one end opened to one side face of the lens frame 202, which is formed at the same position as the one side face on which the lens 203*a* is exposed, and the other end opened to the through-hole 202*i*2, is formed.

Note that in the through-holes 205*i* and 202*i*2, an illumination optical system 204 configured by a light guide 204*b*, and a cover glass 204*a* that abuts on a distal end face of the light guide 204*b* and is exposed on the one side face of the outer circumferential face described above of the cover member 205 is fixed. Note that the illumination optical system 204 has a function of supplying illuminating light to the object located at the radial direction K side with respect to the adapter 1.

Here, in the through-hole 202*i*1, the diaphragm 7 is fixed to a distal end face of the lens 203*d*. Note that the position where the diaphragm 7 is fixed is not limited to the distal end face of the lens 203*d*, but may be fixed to any position with respect to the through-hole 202*i*1. Note that the shape and the function of the diaphragm 7 are the same as the shape and the function of the diaphragm 7 of the aforementioned first embodiment.

Further, in the through-hole 202*i*1, the diaphragm 6 is fixed to a position away from the diaphragm 7 along the optical axis L, more specifically, a position separated from the diaphragm 7 along the optical axis L to sandwich the lens 203*c* and the prism 203*b* between the diaphragm 6 and the diaphragm 7 along the optical axis L, on the optical axis L, more specifically, a position abutting an proximal end face 203*ab* of the lens 203*a*, that is separated from the diaphragm 7 by L5 along the optical axis L.

Note that the position where the diaphragm 6 is fixed is not limited to the position abutting on the proximal end face 203*ab* of the lens 203*a*, but may be any position in the through-hole 202*i*1, if only the position is separated from the diaphragm 7 so that at least one lens is sandwiched between the diaphragm 6 and the diaphragm 7 along the optical axis L.

Note that a method for positioning the diaphragm 6 in the circumferential direction C, the shape and the function are the same as the method, the shape and the function of the diaphragm 6 of the aforementioned first embodiment.

As above, in the present embodiment, it is shown that in the adapter 1, the diaphragm 6 is fixed by being separated from the diaphragm 7 for brightness adjustment by L5 along the optical axis L to sandwich the prism 203*b* and the lens 203*c* between the diaphragm 6 and the diaphragm 7.

According to the above, even if the adapter 1 is a side-view adapter, the image of the outline of the image formation portion 6*v* is clearly formed in the respective regions e1 to e4 of the light receiving section 28*j*, because the diaphragm 6 is located by being separated from the diaphragm 7 by L5 along the optical axis L, and therefore, the CPU 53 does not erroneously recognize the position and the number of the image formation portions 6*v*. Note that the other effects are the same as the effects of the aforementioned first embodiment.

Third Embodiment

Figure 15:
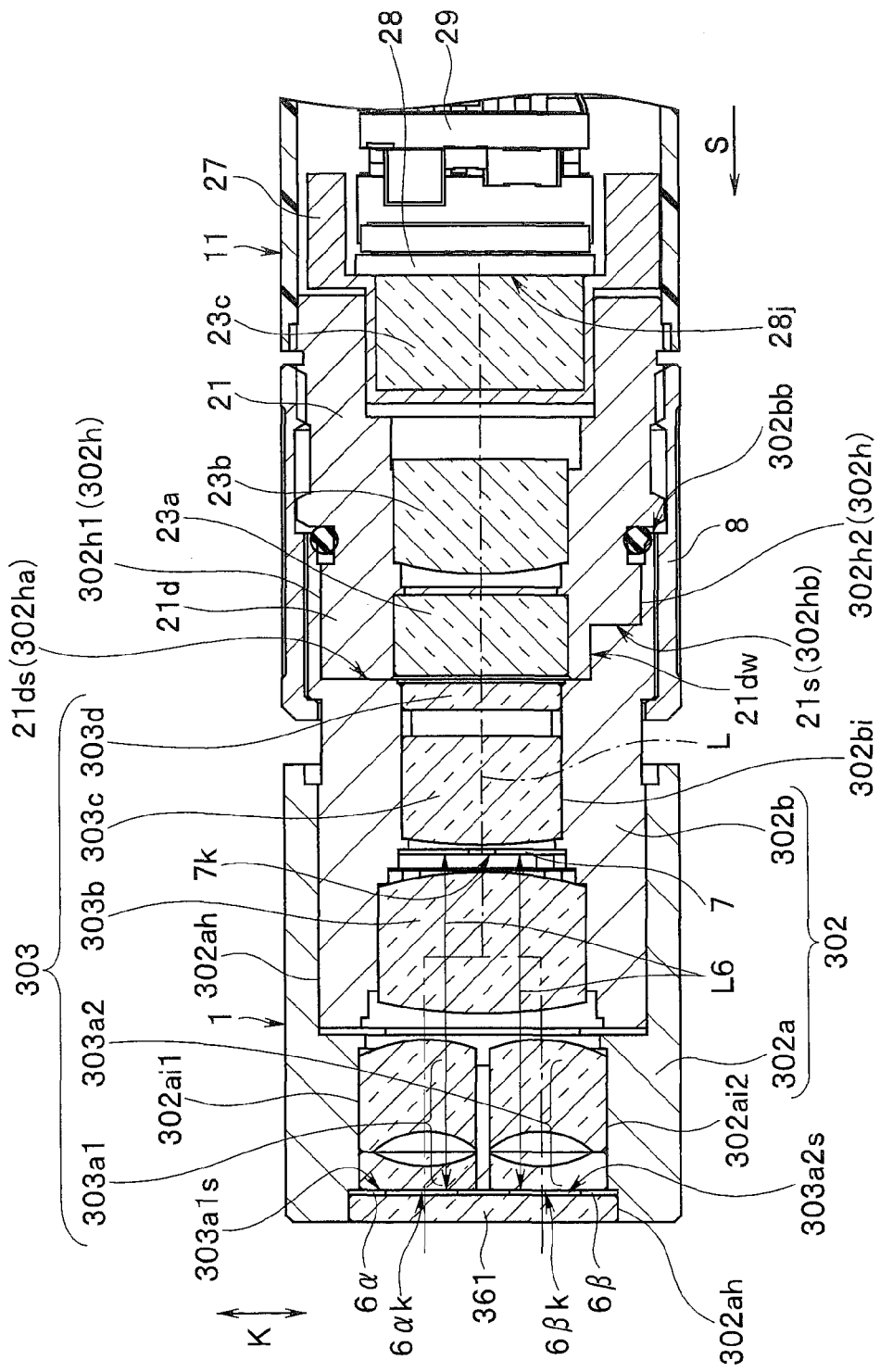
FIG. 15 is a partial sectional view in a state where an adapter is attached to a distal end portion of an insertion portion of an endoscope of a third embodiment.
Figure 16:
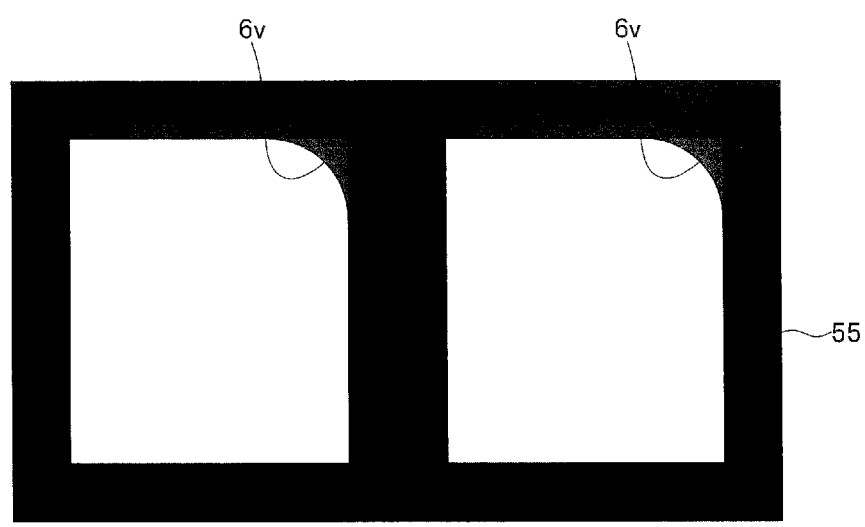
FIG. 16 is a view showing a state where an image formation portion of a diaphragm for type determination is displayed on a monitor in FIG. 1 respectively via respective lenses of a front-view adapter for stereo measurement.

FIG. 15 is a partial sectional view in a state where an adapter is attached to a distal end portion of an insertion portion of an endoscope of a present embodiment, and FIG. 16 is a view showing a state where image formation portions of a diaphragm for type determination are respectively displayed on a monitor in FIG. 1, via respective lenses of a front-view adapter for stereo measurement.

A configuration of an endoscope of a third embodiment differs in that an adapter attachable to and detachable from the distal end portion of the insertion portion is a known front-view adapter for stereo measurement, as compared with the endoscope of the first embodiment shown in FIG. 1 to FIG. 11 described above. Consequently, only the difference will be described, the same components as the components of the first embodiment are assigned the same reference signs, and explanation of the components will be omitted.

Consequently, in the present embodiment, two or more kinds of adapters 1 attachable to and detachable from the distal end portion 11 will be described with front-view adapters for stereo measurement cited as examples. Further, in the present embodiment, explanation will be made such that two or more kinds of front-view adapters for stereo measurement with different diameters and view angles, for example, are attachable to and detachable from the distal end portion 11.

As shown in FIG. 15, the adapter 1 includes a lens frame 302 formed into a substantially columnar shape. The lens frame 302 is configured by a first lens frame 302a and a second lens frame 302b, and a distal end side of the second lens frame 302b is fitted into a concave portion 302ah formed on a proximal end face of the first lens frame 302a, whereby the first lens frame 302a and the second lens frame 302b are connected.

On an outer circumference at a proximal end side of the second lens frame 302b, the retaining ring 8 having a female screw formed on an inner circumferential face is provided.

Further, in the second lens frame 302b, a through-hole 302bi that penetrates through the second lens frame 302b along the insertion direction S is formed.

Further, on a proximal end face 302bb of the second lens frame 302b, a concave portion 302h that is formed to be recessed to a front side along the insertion direction S from the proximal end face 302bb is formed.

The concave portion 302h is configured by a fitting portion 302h2 in which the distal end side of the distal end portion main body 21 is fitted when the adapter 1 is attached to the distal end portion 11, and a fitting portion 302h1 which is formed to be recessed to a front side from the fitting portion 302h2 and in which the convex portion 21d is fitted. Note that the fitting portion 302h1 communicates with the through-hole 302bi.

Further, when the adapter 1 is attached to the distal end portion 11, the distal end face 21ds of the convex portion 21d abuts on a bottom face 302ha of the fitting portion 302h1, and the distal end face 21s of the distal end portion main body 21 faces a bottom face 302hb of the fitting portion 302h2.

Furthermore, in the proximal end side of the second lens frame 302b, at a part of a site where the fitting portion 302h1 is formed, a pin not illustrated that protrudes inward in the radial direction K toward the fitting portion 302h1 is provided, as shown in FIG. 4 described above. The pin is fitted into the groove 21dm which is formed on the outer circumferential face of the distal end portion main body 21 after the female screw of the adapter 1 is screwed onto the male screw of the distal end portion main body 21.

Further, to the through-hole 302bi, lenses 303b, 303c and 303d that are a plurality of optical members are fixed.

In the first lens frame 302a, two through-holes 302ai1 and 302ai2 which penetrate through the first lens frame 302a parallel along the insertion direction S are formed, and the respective through-holes 302ai1 and 302ai2 are opened to the concave portion 302ah which is formed on a distal end face of the first lens frame 302a. Note that a cover glass 361 is fitted in the concave portion 302ah.

Further, to the through-hole 302ai1, a lens 303a1 of a plurality of optical members is fixed, and to the through-hole 302ai2, a lens 303a2 of the plurality of optical members is fixed. Further, the lens 303a1 and the lens 303a2 have a parallax.

Note that a lens unit 303 that observes an inside of an object, more specifically, a front side with respect to the adapter 1 is configured by the cover glass 361, and the lenses 303a1, 303a2, 303b, 303c and 303d. Note that the number of lenses configuring the lens unit 303 is not limited to the aforementioned number.

Consequently, when the adapter 1 is attached to the distal end portion 11, an image of an observation site in the object is formed in the light receiving section 28j of the image pickup device 28 via the cover glass 361, the lenses 303a1, 303b, 303c, 303d and the lens unit 23 on one hand, and is formed in the light receiving section 28j of the image pickup device 28 via the cover glass 361, the lenses 303a2, 303b, 303c and 303d and the lens unit 23 on the other hand, with a parallax from the image passing through the lens 303a1.

That is, the two images having a parallax of the observation site are simultaneously formed respectively in the light receiving section 28j. Consequently, two image formation regions are formed in the light receiving section 28j, and the aforementioned regions e1 to e4 are set at the four corners of the respective image formation regions respectively.

Here, in the through-hole 302bi, the diaphragm 7 is fixed between the lens 303c and the lens 303b. Note that the position where the diaphragm 7 is fixed may be any position with respect to the through-hole 302bi. Further, the shape and the function of the diaphragm 7 are the same as the shape and the function of the diaphragm 7 of the aforementioned first embodiment.

Further, in the through-holes 302bi and 302ai1, a diaphragm 6α is fixed to a position away from the diaphragm 7 along the optical axis L, more specifically, a position separated from the diaphragm 7 along the optical axis L to a front side which is an object side to sandwich the lenses 303a1 and 303b between the diaphragm 6α and the diaphragm 7 along the optical axis L, on the optical axis L, more specifically, a position abutting on a distal end face 303a1s of the lens 303a1, which is separated from the diaphragm 7 by L6 to the front side.

Furthermore, in the through-holes 302bi and 302ai2, a diaphragm 6β is fixed to a position away from the diaphragm 7 along the optical axis L, more specifically, a position separated from the diaphragm 7 along the optical axis L to the front side which is the object side to sandwich the lenses 303a2 and 303b between the diaphragm 6β and the diaphragm 7 along the optical axis L, on the optical axis L, more specifically, a position abutting on a distal end face 303a2s of the lens 303a2, which is separated by L6 from the diaphragm 7 to the front side.

Note that the positions where the diaphragms 6α and 6β are fixed are not limited to the positions abutting on the distal end faces 302a1s and 302a2s of the lenses 302a1 and 302a2, but may be any positions in the through-holes 302ai1 and 302ai2, if only the positions are separated from the diaphragm 7 along the optical axis L so that at least one lens is sandwiched between the diaphragms 6α and 6β and the diaphragm 7, or may be fixed to a rear side from the diaphragm 7. Note that the diaphragms 6α and 6β may be integrally fixed. Further, the image formation portion 6v may be provided at either one of the diaphragm 6α and 6β. Further, the image formation portions 6v may be provided at different positions in the diaphragms 6α and 6β. The effect of increase of the number of adapters that can be determined is provided.

Further, a method for positioning the diaphragms 6α and 6β in the circumferential direction C, the shapes and the functions are the same as the method, the shape and the function of the diaphragm 6 of the aforementioned first embodiment.

As above, in the present embodiment, it is shown that in the adapter 1, the diaphragm 6α is fixed by being separated from the diaphragm 7 for brightness adjustment by L6 along the optical axis L to sandwich the lenses 303b and 303a1 between the diaphragm 6α and the diaphragm 7.

Further, it is shown that, the diaphragm 6β is fixed by being separated from the diaphragm 7 for brightness adjustment by L6 along the optical axis L to sandwich the lenses 303b and 303a2 between the diaphragm 6β and the diaphragm 7.

According to the above, even if the adapter 1 is a front-view adapter for stereo measurement, the images of the outline of the image formation portion 6v are clearly formed in the respective regions e1 to e4 which are respectively provided in the image formation regions for the two images of the object having a parallax formed by the lenses 303a1 and 303a2 in the light receiving section 28j, as shown in FIG. 16, because the diaphragms 6α and 6β are located by being separated from the diaphragm 7 by L6 along the optical axis L, and therefore, the CPU 53 does not erroneously recognize the positions and the number of the image formation portions 6v. Note that the other effects are the same as the effects of the aforementioned first embodiment.

Fourth Embodiment

Figure 17:
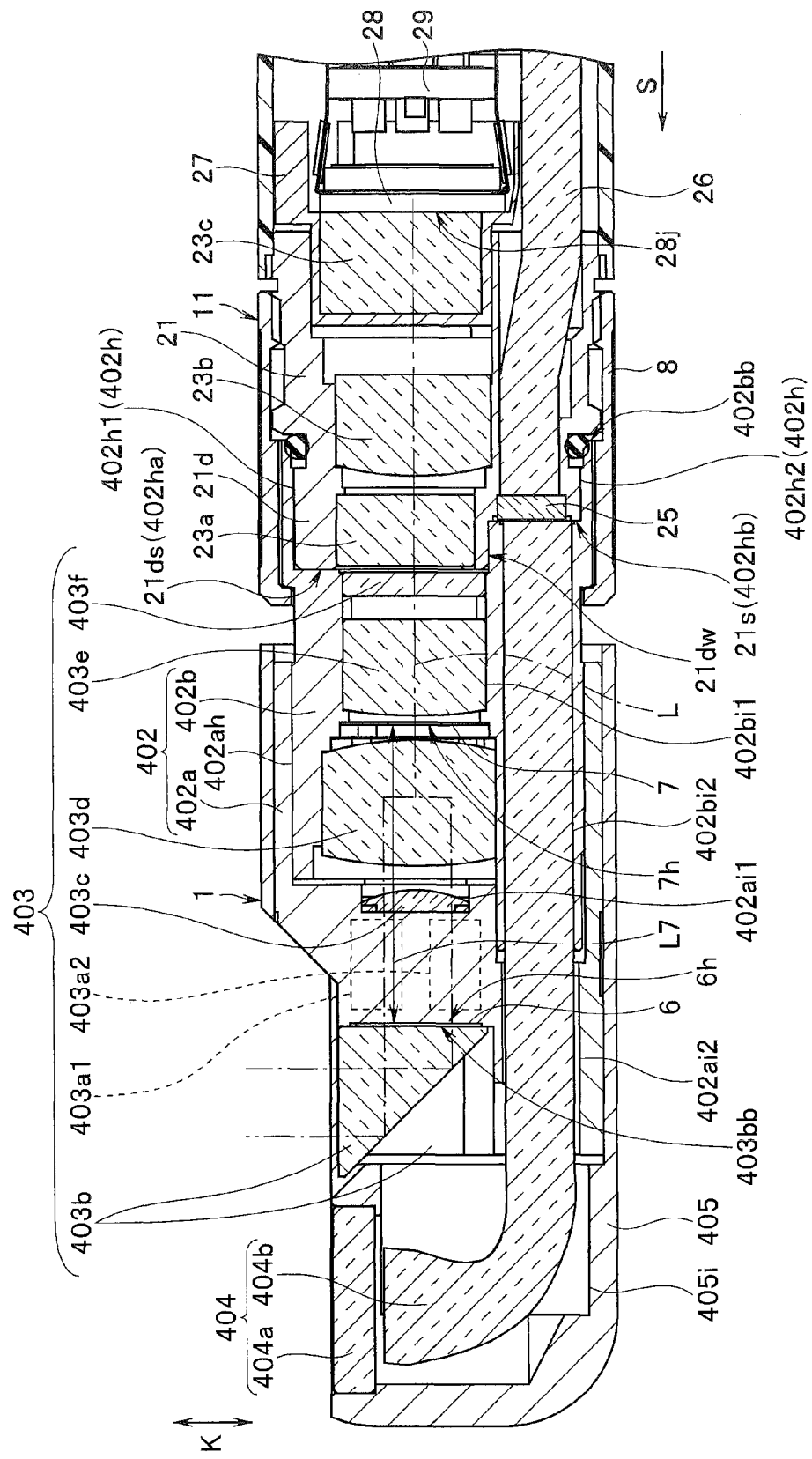
FIG. 17 is a partial sectional view in a state where an adapter is attached to a distal end portion of an insertion portion of an endoscope of a fourth embodiment.

FIG. 17 is a partial sectional view in a state where an adapter is fitted to a distal end portion of an insertion portion of an endoscope of a present embodiment.

A configuration of an endoscope of the fourth embodiment differs in that an adapter attachable to and detachable from the distal end portion of the insertion portion is a known side-view adapter for stereo measurement, as compared with the endoscope of the third embodiment shown in FIG. 14 described above. Consequently, only the difference will be described, the same components as the components of the third embodiment are assigned the same reference signs, and explanation of the components will be omitted.

Therefore, in the present embodiment, two or more kinds of adapters 1 attachable to and detachable from the distal end portion 11 will be described with side-view adapters for stereo measurement cited as examples. Further, in the present embodiment, explanation will be made such that two or more kinds of side-view adapters for stereo measurement with different diameters and view angles, for example, are attachable to and detachable from the distal end portion 11.

As shown in FIG. 17, the adapter 1 used in the present embodiment includes a lens frame 402 formed into a substantially columnar shape. The lens frame 402 is configured by a first lens frame 402a and a second lens frame 402b, and a distal end side of the second lens frame 402b is fitted into a concave portion 402ah formed in a proximal end face of the first lens frame 402a, whereby the first lens frame 402a and the second lens frame 402b are connected.

On an outer circumference at a proximal end side of the second lens frame 402b, the retaining ring 8 having a female screw formed on an inner circumferential face is provided.

In a proximal end face 402bb of the second lens frame 402b, a concave portion 402h that is formed to be recessed to a front side along the insertion direction S from the proximal end face 402bb is formed.

The concave portion 402h is configured by a fitting portion 402h2 in which the distal end side of the distal end portion main body 21 is fitted when the adapter 1 is attached to the distal end portion 11, and a fitting portion 402h1 which is formed to be recessed to a front side from the fitting portion 402h2 and in which the convex portion 21d is fitted.

Further, when the adapter 1 is attached to the distal end portion 11, the distal end face 21ds of the convex portion 21d abuts on a bottom face 402ha of the fitting portion 402h1, and the distal end face 21s of the distal end portion main body 21 faces a bottom face 402hb of the fitting portion 402h2.

Furthermore, in the proximal end side of the second lens frame 402b, at a part of a site where the fitting portion 402h1 is formed, a pin not illustrated that protrudes inward in the radial direction K toward the fitting portion 402h1 is provided as shown in FIG. 4 of the aforementioned first embodiment. The pin is fitted into the groove 21dm (see FIG. 4) formed on the outer circumferential face of the distal end portion main body 21 after the female screw of the adapter 1 is screwed onto the male screw of the distal end portion main body 21.

Further, in the second lens frame 402b, a through-hole 402bi1 that penetrates through the second lens frame 402b in the insertion direction S is formed. To the through-hole 402bi1, lenses 403d, 403e and 403f that are a plurality of optical members are fixed.

Furthermore, in the second lens frame 402b, a through-hole 402bi2 that penetrates through the second lens frame 402b in the insertion direction S is formed.

Further, in the first lens frame 402a, through-holes 402ai1 and 402ai2 that penetrate through the first lens frame 402a along the insertion direction S are formed.

To the through-hole 402ai1, lenses 403a1 and 403a2, a lens 403c and a prism 403b that are a plurality of optical members are fixed. Note that the lenses 403a1 and 403a2 are provided in parallel in a depth direction of FIG. 17. Further, the lens 403a1 and the lens 403a2 have a parallax. Further, the prism 403b is exposed on one side face of the outer circumferential face of the adapter 1.

Further, the outer circumference at the distal end side of the first lens frame 402a is covered with a cover member 405. In the cover member 405, an L-shaped through-hole 405i having one end opened to one side face which is formed at the same position as the one side face on which the prism 403b described later is exposed, in an outer circumferential face of the cover member 405, and the other end opened to the through-hole 402ai2 is formed.

Note that in the through-holes 405i, 402ai2 and 402bi2, an illumination optical system 404 configured by a light guide 404b, and a cover glass 404a that abuts on a distal end face of the light guide 404b and is exposed on the one side face of the outer circumferential face described above of the cover member 405 is fixed. Note that the illumination optical system 404 has a function of supplying illuminating light to the object which is located at the radial direction K side with respect to the adapter 1.

Note that a lens unit 403 that observes an inside of the object, more specifically, an observation site located at the radial direction K side with respect to the adapter 1 is configured by the lenses 403a1 and 403a2, the prism 403b and the lenses 403c, 403d, 403e and 403f. Note that the number of lenses that configure the lens unit 403 is not limited to the aforementioned number.

Consequently, when the adapter 1 is attached to the distal end portion 11, an image of the observation site inside the object is formed in the light receiving section 28*j* of the image pickup device 28 via the prism 403*b*, the lens 403*a*1, and the lenses 403*c*, 403*d*, 403*e* and 403*f* on one hand, and is formed in the light receiving section 28*j* of the image pickup device 28 via the prism 403*b*, the lens 403*a*2, and the lenses 403*c*, 403*d*, 403*e* and 403*f* on the other hand, with a parallax from the image passing through the lens 403*a*1.

That is, the two images having a parallax of the observation site are simultaneously formed respectively in the light receiving section 28*j*. Consequently, two image formation regions are formed in the light receiving section 28*j*, and the aforementioned regions e1 to e4 are respectively set at the four corners of the respective image formation regions.

Here, in the through-hole 402*bi*1, the diaphragm 7 is fixed between the lens 403*d* and the lens 403*e*. Note that the position where the diaphragm 7 is fixed may be any position with respect to the through-hole 402*bi*1. Note that the shape and the function of the diaphragm 7 are the same as the shape and the function of the diaphragm 7 of the first embodiment described above.

Further, in the through-hole 402*ai*1, the diaphragm 6 is fixed to a position away from the diaphragm 7 along the optical axis L, more specifically, a position separated from the diaphragm 7 along the optical axis L to sandwich the lenses 403*a*1, 403*a*2, 403*c* and 403*d* between the diaphragm 6 and the diaphragm 7 along the optical axis L, on the optical axis L, more specifically, a position abutting on an proximal end face 403*bb* of the prism 403*b*, which is separated from the diaphragm 7 by L7 along the optical axis L.

Note that the position where the diaphragm 6 is fixed is not limited to the position abutting on the proximal end face 403*bb* of the prism 403*b*, but may be any position in the through-hole 402*ai*1, if only the position is separated from the diaphragm 7 along the optical axis L so that at least one lens is sandwiched between the diaphragm 6 and the diaphragm 7.

Note that a method for positioning the diaphragm 6 in the circumferential direction C, the shape and the function are the same as the method, the shape and the function of the diaphragm 6 of the aforementioned second embodiment.

As above, in the present embodiment, it is shown that in the adapter 1, the diaphragm 6 is provided by being separated from the diaphragm 7 for brightness adjustment by L7 along the optical axis L to sandwich the lenses 403*a*1, 403*a*2, 403*c* and 403*d* between the diaphragm 6 and the diaphragm 7.

According to the above, even if the adapter 1 is a side-view adapter for stereo measurement, the image of the outline of the image formation portion 6*v* is clearly formed in the respective regions e1 to e4 which are respectively provided in the image formation regions for the two images of the object having a parallax, which are formed by the lenses 403*a*1 and 403*a*2 in the light receiving section 28*j*, because the diaphragm 6 is located by being separated from the diaphragm 7 by L7 along the optical axis L, and therefore, the CPU 53 does not erroneously recognize the position and the number of the image formation portions 6*v*. Note that the other effects are the same as the effects of the aforementioned second embodiment.

Further, in the aforementioned first to fourth embodiments, industrial endoscopes are shown by being cited as examples, but it is needless to say that the present invention may be applied to medical endoscopes.

What is claimed is:
1. An endoscope comprising:
    two or more types of adapters;
    an insertion portion comprising a distal end portion located at a distal end in an insertion direction of the insertion portion, wherein the distal end portion is configured to be attachable to and detachable from individual ones of the two or more types of adapters;
    a plurality of optical members provided in each of the two or more types of adapters;
    a diaphragm for brightness adjustment that is opened on an optical axis of the plurality of optical members in the each of the two or more types of adapters;
    an image sensor that is provided in the distal end portion, wherein the image sensor comprises a light receiving surface on which an image of an object is formed via the plurality of optical members in any one of the two or more types of adapters attached to the distal end portion of the insertion portion;
    a diaphragm for type determination that is opened on the optical axis in the each of the two or more types of adapters at a position separated from the diaphragm for brightness adjustment to sandwich at least one of the optical members between the diaphragm for type determination and the diaphragm for the brightness adjustment along the optical axis,
    wherein the diaphragm for type determination comprises one or more image forming surfaces an image of which is formed on the light receiving surface, and a position and a number of the one or more image forming surfaces provided for the diaphragm for type determination differ according to the type of the two or more types of adapters; and
    a processor comprising hardware, wherein the processor is configured to determine a type of the each of the two or more types of adapters by determining the position and the number of the one or more image forming surfaces the image of which is formed on the light receiving surface of the image sensor.
2. The endoscope according to claim 1,
    wherein the one or more image forming surfaces are provided to protrude to an opening of the diaphragm for type determination.
3. The endoscope according to claim 2,
    wherein the one or more image forming surfaces have a site in a partial circular arc shape with a center of the light receiving surface of the image sensor as a center of a circle.
4. The endoscope according to claim 2,
    wherein in the image sensor, an external shape of the light receiving surface is formed into a rectangular shape, and an image of the one or more image forming surfaces is formed in at least one region out of regions in four corners of the light receiving surfaces.
5. The endoscope according to claim 4,
    wherein the regions in the four corners in which the image of the one or more image forming surfaces is formed in the light receiving surface of the image sensor are four regions which are respectively formed between an inscribed circle on one side of the light receiving surface having the rectangular external shape, with a center of the light receiving surface as a center of the circle, and the four corners of the light receiving surface.
6. The endoscope according to claim 4,
    wherein the regions in the four corners in which the image of the one or more image forming surfaces is formed in the light receiving surface of the image sensor are set within two regions which are respectively formed between an inscribed circle on one side of an effective pixel region of the light receiving surface smaller in external shape than the light receiving surface and having a rectangular external shape, with a center of the light receiving surface as a center of the circle, and the four corners of the light receiving surface.

7. The endoscope according to claim 4,
wherein the processor is configured to determine that the individual ones of the two or more types of adapters are in a state unattached to the distal end portion when the image of the one or more image forming surfaces is in a state unformed in all the regions of the regions in the four corners of the light receiving surface.

8. The endoscope according to claim 4,
wherein the processor is configured to not perform determination of the type of the each of the two or more types of adapters, when the image of the one or more image forming surfaces is formed in each of all of the regions of the regions of the four corners of the light receiving surface.

9. The endoscope according to claim 1,
wherein the diaphragm for type determination is provided at the object side from the diaphragm for brightness adjustment along the optical axis.

10. The endoscope according to claim 1,
wherein the diaphragm for type determination is provided for any one lens of a plurality of lenses comprising the plurality of optical members provided in the each of the two or more types of adapters.

11. The endoscope according to claim 10,
wherein the diaphragm for type determination is integrally formed by being vapor deposited onto the any one lens.

12. The endoscope according to claim 1,
wherein the diaphragm for type determination comprises a flare diaphragm that narrows down light forming an image in the image sensor via the plurality of optical members.

13. The endoscope according to claim 1,
wherein the diaphragm for type determination is provided separately from a flare diaphragm that is opened on the optical axis of the plurality of optical members in the each of the two or more types of adapters, and narrows down light forming an image in the image sensor via the plurality of optical members.

* * * * *